(12) United States Patent
Yoon et al.

(10) Patent No.: US 11,213,050 B2
(45) Date of Patent: Jan. 4, 2022

(54) ESCHERICHIA COLI BACTERIOPHAGE ESC-COP-9 AND USE FOR INHIBITING PROLIFERATION OF PATHOGENIC ESCHERICHIA COLI THEREOF

(71) Applicant: INTRON BIOTECHNOLOGY, INC., Gyeonggi-do (KR)

(72) Inventors: Seong Jun Yoon, Seoul (KR); Soo Youn Jun, Seoul (KR); Hyoun Rok Paik, Incheon (KR); Jee Soo Son, Seoul (KR); Sang Hyeon Kang, Seoul (KR)

(73) Assignee: INTRON BIOTECHNOLOGY, INC.

( * ) Notice: Subject to any disclaimer, the term of this patent is extended or adjusted under 35 U.S.C. 154(b) by 21 days.

(21) Appl. No.: 16/464,872

(22) PCT Filed: Sep. 29, 2017

(86) PCT No.: PCT/KR2017/010957
§ 371 (c)(1),
(2) Date: May 29, 2019

(87) PCT Pub. No.: WO2018/101595
PCT Pub. Date: Jun. 7, 2018

(65) Prior Publication Data
US 2019/0321423 A1    Oct. 24, 2019

(30) Foreign Application Priority Data

Nov. 30, 2016 (KR) .................. 10-2016-0161324

(51) Int. Cl.
| | | |
|---|---|---|
| A23K 10/16 | (2016.01) | |
| A23K 30/18 | (2016.01) | |
| A61K 35/76 | (2015.01) | |
| C12N 7/00 | (2006.01) | |
| A01N 63/40 | (2020.01) | |

(52) U.S. Cl.
CPC ............. *A23K 10/16* (2016.05); *A01N 63/40* (2020.01); *A23K 30/18* (2016.05); *A61K 35/76* (2013.01); *C12N 7/00* (2013.01); *C12N 2795/10332* (2013.01)

(58) Field of Classification Search
CPC ........ A01N 63/00; A01N 63/60; A01N 63/50; A01N 63/20; A01N 63/40; A23K 10/16; A23K 10/18; A23K 20/147; A23K 20/163; A23K 30/18; A23K 50/30; A23K 50/60; A61K 35/76; A61K 2300/00; A61K 31/7105; A61K 31/711; A61K 35/74; A61K 2035/11; A61K 45/06; A61K 48/005; A61K 9/7007; A61K 38/164; A61K 2039/5158; A61K 2039/552; A61K 2039/55505; A61K 2039/55566; A61K 2039/6006; A61K 2039/70; A61K 39/0011; A61K 39/0225; A61K 39/0275; A61K 39/12; A61K 38/465; A61K 9/0014; C12N 2795/10321; C12N 2795/10332; C12N 7/00; C12N 2795/00032; C12N 15/70; C12N 15/902; C12N 1/20; C12N 2310/20; C12N 2795/10132; C12N 15/102; C12N 15/113; C12N 15/746; C12N 2320/31; C12N 9/16; C12N 2795/00051; C12N 15/1131; C12N 1/38; C12N 2310/10; C12N 2710/16122; C12N 2710/16222; C12N 2710/16334; C12N 2795/00021; C12N 2800/80; C12N 2795/10121; C12N 2795/10122; C12N 2795/10322; C12N 15/74; C12N 9/22; Y02A 50/30; Y02A 50/482; C08L 77/12; A61L 15/225; A61L 15/26; A61L 26/0019; A61L 26/0052; A61L 2300/404; A61L 26/0066; A61L 15/38; A61L 15/44; A61L 2/00; A61L 2/0005; A61L 2/18; A61L 2/22; A61L 26/0057; A23B 4/22; A23B 7/155; A23B 4/20; A23B 5/16; A23B 7/154; A23G 9/30; A23L 3/34635; A23L 3/3571; A23L 3/3463; A23L 3/3472; C08G 69/44; A61P 31/04; A61P 17/02; A61P 31/02; A61P 31/06; A61P 35/00; A61P 43/00; A23V 2002/00; A23V 2200/32
See application file for complete search history.

(56) References Cited

U.S. PATENT DOCUMENTS

| | | | |
|---|---|---|---|
| 10,265,354 | B2 | 4/2019 | Yoon et al. |
| 10,265,355 | B2 | 4/2019 | Yoon et al. |

FOREIGN PATENT DOCUMENTS

| | | |
|---|---|---|
| KR | 10-2011-0041670 A | 4/2011 |
| KR | 10-2016-0080575 A | 7/2016 |
| WO | WO-2016/108541 A1 | 7/2016 |

OTHER PUBLICATIONS

Kulikov et al. "Genomic sequencing and iological characteristics of a novel *Escherichia coli* bacteriophage 9g, a putative representative of a new Siphoviridae genus," Published Dec. 19, 2014, Viruses, 6: 5077-5092 (Year: 2014).*

(Continued)

*Primary Examiner* — Deborah K Ware
(74) *Attorney, Agent, or Firm* — Ballard Spahr, LLP

(57) ABSTRACT

The present invention relates to a Siphoviridae bacteriophage Esc-COP-9 (Accession number: KCTC 13131BP) isolated from nature, which has the ability to specifically kill *Escherichia coli* and which includes a genome expressed by SEQ. ID. NO: 1, and to a method of preventing and treating a pathogenic *Escherichia coli* infection using a composition including the same as an active ingredient.

2 Claims, 1 Drawing Sheet
Specification includes a Sequence Listing.

(56) References Cited

OTHER PUBLICATIONS

Jun, J.W et al., Characterization and Complete Genome Sequence of the Shigella Bacteriophage pSF-1. Res Microbiol. 2013; 164:979-86.
NCBI, GenBank Accession No. KC710998.1 (Dec. 13, 2013) (32 pages).
International Search Report and Written Opinion dated Feb. 19, 2018 by the International Searching Authority for Patent Application No. PCT/KR2017/010957, which was filed on Sep. 29, 2017 and published as WO 2018/101595 on Jun. 7, 2018 (Inventor—Yoon et al.; Applicant—Intron Biotechnology Co., Ltd.) (Original—7 pages; Translation—3 pages).

* cited by examiner

[FIG. 1]
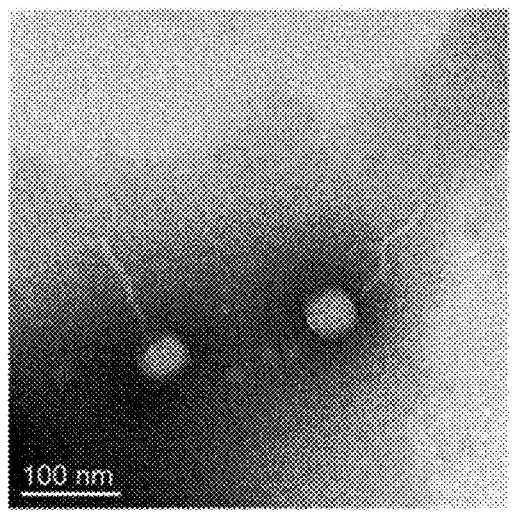
[FIG. 2]
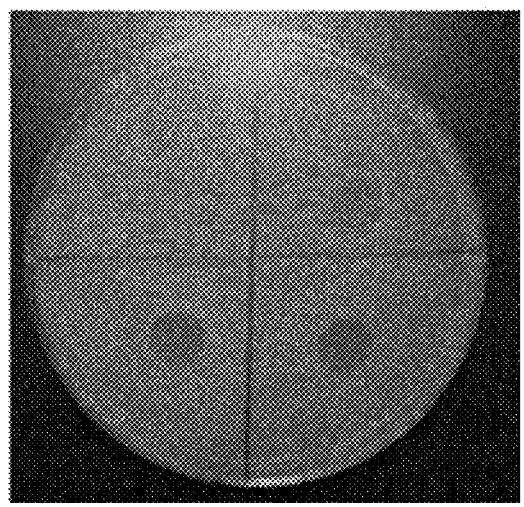

SEQUENCE LISTING

<160> NUMBER OF SEQ ID NOS: 1

<210> SEQ ID NO 1
<211> LENGTH: 51102
<212> TYPE: DNA
<213> ORGANISM: Bacteriophage Esc-COP-9

<400> SEQUENCE: 1
atattgaaac agcttttgac cttgcgaagc agtctgataa aatggcggcg cagcgtaaat    60

```
ctgttaaggg cgattctttc gagtctggca agagtgaaaa aaccgactcc cttgatccga      120
ctgcgcgttt gaaaaaactt aaataaggag aaataaacat ggctacaatt ggagcaagtt      180
attttgctgt aatgtctcgt gcgttacctg gtcaggtttc tgacacttca gcttataata      240
ttgatggcgc ttgtgttctt gagaatgcgg aaggaaacca aacaaaaac attttgttg       300 gtgttgcagt ccagcatggc ggcgttgatg ctatgggcaa taagctaatt aagccgatgg      360
cggcaagcgg caaggcttac ggtgttgcaa ttcgatccca cttccagacg acttcggctg      420
acggtcgaat gatttatgag tctggcggcg gaatcaacgt aatgactgag gggcgtgttt      480
ggatgttggc taaagacgct ccgcaccag cgttcggcgc tacaatcaaa ctgtctgatg       540
atggtcaggt tgataccgcg tctggtacta tcgaaaccaa ctggatcgcg actggtgatt      600
tcaccaagtt tcaagacttg aagctggtag aggttcaggt acaaaaagtt ccggcagttt      660
cagcagttta ataaatatgg cgctcactga gcgcctttt tatatttggg gttatcatga       720
gtgattattc agtcattgtt ggcgctgagt cgccagggtg catggtcgat tcttcaataa      780
tggtgattaa cggatctttc gtgtgcggag atgaatttat tgagccaggt aagattgtgc      840
gactatcaca tataacaaat ggatacaaaa tagcaagtgt taatggggat ctcgttattg      900
gtgtggcagt aaggccgccg gactcgtgca tatatgagga gggtgatccc gttagtgtag      960
ttagtagagg tagtgtgtgg tgcttaactt ctgagagcga agcgccagaa tatggagata     1020
aagtatttgt aacgcaagat ggagatgcgg catacagtga aggcgacttg ctgattggtt     1080
ggatctttac tggcgaacat gtaaaggttg atcatgagtc atatattgtc ggggtaagca     1140
ttagcgcata acacaaaatt atgttgcacg tttaacaaaa aatgctatca ttggggcgtt     1200
acatactaac agcctttata tatggaggaa gaaaatggaa aaagaaaaat ttgatcagct     1260
agatgcggat attgtttcta gctatctggc tactcgcggc gttaagggtg atgcttctga     1320
tatgggtatc tggacggcgc aagagcttca caagatccgc tctaatgctt acgaaaaga      1380 atatccggca ggttcagcgc ttcgtgtatt ccctgtaact aatgagcttt ctgatactga     1440
taagactttt gaatatcaga tgtttgacaa ggttggttac gcaaaaatta tcgctgatta     1500
caccgacgac ctaccgaccg ttgacgcgct gatgtcaagc gaatttggta aagtgttccg     1560
cctgggtaac gcgttcttga tctccattga cgaaatcaag gctggtcagc gtactggcaa     1620
gagcctttcc actcgcaagg caaacgcagc gcaaaacgct catgatcagg aagttaaccg     1680
cctggtgttt aagggttcaa agccgcataa gattctttcg gtgttcgaac atcctaacct     1740
gacaaagatc gtgtcaactg gctggttaag tgctgatgaa acactaagt cccgcaggc       1800 agcatctgat gaactggaaa aggctattga aaccattcag accatcacca atggtcagca     1860
ccgagcaacc aacatcctga ttccgccatc tatgcgcaag gttctttccg ttcgaatgga     1920
aaacaccact gaaagttatc tggaatactt ccagaaacaa aacagcggaa tcaccattga     1980
ctcaatcgca gagcttgagg atattgatgg cacaggaacg aaaggttgcc tggtatatga     2040
gaaagacccg atgaacatgt cgatcgaaat tccagaagca tttaacatgc ttcctgcgca     2100
accaaaagat ctgcatttca agttccgtg tacttcaaaa tgtactggcc tgacgattta      2160
ccgtccgttt acgctagtgc ttattactgg cttgaaaaaa ccaagttaat cgtataacat     2220
tggggaatcc ttaactggat tccctttttt ttattggagg ttatgaaatg gctaaagaaa     2280
aaactgtaac gctaaaggtt tccggcgtgt gccttatcat tgttgatggt gagcattatc     2340
atccaggcaa agagtttgac gtagaagaat caaaattgaa aacaagcgcg tttgaatatc     2400
```

```
taattgcaaa aggcgatctt gaggttaaag acaactccgc attgaacgaa gaaatcaaac    2460
agagcgcagc aagcaaacgt aaaaaagacc cgcgagaggg caagagcaaa gccgaacttg    2520
aagacggcgg catctattaa taaagagggc gcttatagcg ccctttgtca tatctggagg    2580
aaacaaaatg gttgatgaat ttttcactga cgcagaaatc acgcagcaaa tcgtgaaatt    2640
agctccaccg atgaaacaga ttgatccaga tttaatggtg gcatggattg atctagcaaa    2700
ggaatttgtt tgcaagaagc ggtttaaaga atcatatcct aaagcggttg ccctttatac    2760
tttgcacctt atgacgcttg atggagctat gaagcaagaa ggggaaggcg tagagagtta    2820
ctcacggcgc gtggcgtcat tttccctgac tggtgaattt agccagacat ttgatcgcgt    2880
gtccggcgat tcaagcggaa aagagattag acaaactccg tggggcaaaa tgtatgagac    2940
gttaaataga aaaaaaggcg gtggatttgg ccttgtgact ggattccgga ggcgctgcaa    3000
atgaactata acgagatcgc aagaatggca accgaaggaa ttaacttctt tagtgatagc    3060
aacggtgagt ttaagtgcat aacgcagcgt ggaagcgttg aaataatcgg aggcgaagaa    3120
gtacaaaagc cagagattag tgtaatgatt aaaggtttaa ttcgctcacc aaaagtacgc    3180
gaggttgacg gcgagacaat acgagtaaac gataagctgg gagttttcaa caataatgtt    3240
gaaattaaga acgggtatca tattgatgtt gatggtgaat tatatgttgt agttgaagca    3300
agaccaatca gacaaaccaa tgtcacagtt gcttatcggc ctattttgag aaggatttcc    3360
gtgcatggct aaaaactaca cgataaggga atttcatggc aacattgatg cgtggataaa    3420
cgccgttgat aatggactaa aagattgcgt ggaattgttc gccgaaaaag tacacacaga    3480
tttggttaag cgttctcctg tagatactgg tcgttaccgt gcaaactggc aggtaacagc    3540
aaacaatccg ccattgtatg cgcttaacca gtacgataag cacggcgaca aaacgatcgc    3600
ggaaggcaag cgcgccatat acgcaatatt acgaggtggc ggagcagtaa gagccattta    3660
ttttttccaat atgcttattt atgctaacgc gcttgagtac ggtcattcaa acaagcgcc    3720
agcgggtgtg cttgggattg tagctgttaa gttgagatct tatatggctg aagcaataaa    3780
agagtcgagg gctaaaaatg cactatgaat taatgctatc ggcgcgtaag gcgctggcga    3840
ctgaatacga aagcagattc atgatcgctt atgaaaacgt agagtttacg ccacctggtg    3900
acggttcgcc gtggttgaag tttgactatg ccgaagttga cacagaatac ttgtcattgg    3960
atcgcaaatg cgtttcttat atcggaatga ttcaggttgg tattgtgttt ccaccaggtt    4020
acggaactga caggccgcgc gttctcgcta aagagattgc gcaattcttt tacgatggta    4080
aaatgctgga gcatggttat atatatgagg gtgcaagagt tcacaagccg ctcaagagtg    4140
aaagcggttg gattctccca ataaggtttt atgttcgaat tgaaacaaag gagtaaaaat    4200
tatgcattta ccaaatggat cgcaaatttt cgttgagagc aatcgcggaa gcgaaatcca    4260
agcaacagca gtgtcaaacg ccaaagatcc tgttttcact gttgcatctg cggcactgc    4320
gtacaagaaa ggtgattatg tgatcatcac tgcgtcttct tggggtaagc tgattgatcg    4380
tgttatgcgt gtaaaggcta acggtgaaga aacaagcgtg actcttgaag gcgtagatac    4440
tactgatcag aacgttttcc cgactggcgg cactgcatct tttgccaaaa ttgatgcatg    4500
gactgagatc ccttgcgttc aagatttgtc gcaggacggc ggcgaacagc aatactacac    4560
ttatcagtgt ttggcagacg atcaggaaca gcagttacct acctataaga gcgccgtttc    4620
tcttacctac acttttgcgc acgaatacga taacgcgatc tatccgctat tgcgttcagc    4680
agatgaatca ggcgaagtaa ccgctcttcg catgtatgta ccaaaagcaa aagagatgcg    4740
ttgctgggct ggtgtgcttt cgtttaacga aatcccgcag accacagtta acgaaatgga    4800
```

-continued

```
aactgtttcc ctttctgtat cactgaaagg tcgattcacc tttctaccct ctcaagtaga   4860
gtaataacaa ggggcattgc gcccctttt  ttgttactgt acaatcatga tacacgattc   4920
ataatcaatt cttttaacaa aaagtgctat caaggagaaa gaaatgtcaa aaatgaaatt   4980
gacgattggg ccgcttcctg actttaaatt accagtgaaa tttgcaatgc ctaacgagaa   5040
agatcaaaca attatcttca cagttcgcca ccgcaaaaca agtgagattc acgagcgcta   5100
cacgtcagat actccaatga gcgatgttga aatgatcacc ttccttgctt ccggttggaa   5160
tcttgatgat gaatttaacg aagaaaatat taaacagctt cttgattact acccagcgac   5220
agcaatcgga ttaactagcg catacatgaa agcgcttgcg gggcagcgag taaaaaacta   5280
aaaagggcgg tttacctgtt ttatcagaaa ccgccgacag atgcagagct tgaggccgtt   5340
ggccttacaa gggcagacta tgaaggagaa gatccgccag aggttatatt tgatgaaagc   5400
atgatgcaat catgggatat attttgcgca atgcaaacgc aatggagatg ttcaggcggt   5460
ggcgcttacg gatttgatta taacgtcttg cctatgcttt ttgagattta caaggttgag   5520
gatcgcgaga tggcgctaaa cgacttgcga atcatggagc aaaaagcact tgaaatgatg   5580
cattcaaaat aagcgcctac gggcgctttt ttattacctg gaggattaat aatgtcagaa   5640
caatacgcag gcttgacgct tggggttgat gtttctcaac tcaacaatgc tgtaaagtct   5700
ttgcagcaat tcaaaaaggc aaacgacgat gcaaagggaa gcgttgagag ttttgttgat   5760
tcagaggttg ttgcaagaca aagagccaaa caactggctg aggaattggc aaagcagaag   5820
caagaattta aagcaattca gtcggcaata gatccgacag caagcaaaat ggataagttg   5880
cgccaggctg cgacacagct tgatgcgctt tggaaaaaag gaattgtgcc ggatgataca   5940
ttctttgagt taggatcaat tcttgagacg cagcaaaaca aactgatcgc aactaaaaag   6000
gcgctaactg aagaaggccg cgcggcgctt gaggaagcaa aaaacaaggc aagggcagag   6060
gctgaggcaa gaaagtttat tgcggcattg caggcgcaag ctgacgcagc ggaaaaaaca   6120
aaatcagagc ttgtcgaaat gagagccgca caacttggag ttagtgcaga ggctgcgcca   6180
tttattgcaa aaatgaagga gcaggaaaaa caagcctcaa aacttggcgt ttctatgggg   6240
cagtacaagc aagcaatggc gcaattgcca atgcagatca ctgacgttgt tacttctctt   6300
gcttcaggaa tgccagtatg gatgatcgca atccagcagg gcgggcagat caaggactca   6360
ttcggcggtg ttgctaatac ttttaaagcg ctaatgacat ttgtcacgcc gctaagtgtt   6420
ggaatgacgg cgctgactgg tgctcttggg tatgcagcat ataacgctta caaagccaac   6480
gcacaactga aggagatcac aaaaaccgtt caggatgcaa caggtctttc cggtgagttt   6540
gcagagcgga tcgcaactgg aatccaggcg ctatctgaca agacaggaga gagcgcagac   6600
aatatcgcaa aggcttacat aagcactaag gatggagcaa gcgaggctat acaaaaactc   6660
gtcgatgttg gatttaccta tgacgaagca aaggcaaaag taaacgaata caaaaacgca   6720
tcaagttttg taagtcttaa caatgaaatt gctgatcaca aaaacaaagt tcttgagctt   6780
ggcgattcat ggtatgcggt cttaaaagca aaacgtgatt atgcttcacc gtccggcggg   6840
ctgttgggga aagagcttgg ttatgtgaat ccaatgctgc aatttgcgaa gaacacctat   6900
gaggatatag gaaagatagt aaaagatgcg aataaggata tggcggaacg agcagcacgc   6960
atcgacagag aaaatctttc attaaacaga gttcgagcgg cgcaagaggc tttaaacaaa   7020
gccatagagg atcagaagaa cgtagcaagg acagcagacg aagagttgaa aaagcgcgcg   7080
gctgagaacg tggagttcag gcgaaaagag cttgaagagg cgaagaaggc gcagcagcaa   7140
```

```
aaggagaaag ttggtggagt tgtaaaagca ccaacagagc agcttgataa ggagctatat   7200
gttctcaagg cgcaacttga aacgctgaaa gagcaccgaa ctgtaaatga tgttatttca   7260
cgccagaggc aatctttgtg gagcattgaa aagcagatcc agatccttga ggaagcgcaa   7320
agtaaacgca agctgacaaa agcggaacag gcgttactaa acgagcaaaa agcagttatt   7380
gctatggcaa aagaaaaggc agagataggc gatcagattg ttttgcaaca gagaaagaac   7440
aagcaatacc aggaagggct taaattcatt cagcaaacat cagatgctat tgacgctatg   7500
aacttgcgac agtctggagc tacagatctg caaatccagc gagagcttga gttgaagaag   7560
ttgcgaactg attatgttgc tggcggcggt agtatcgacg atgaaattta tcagcagatg   7620
gaagcaaagc tgaaggagta ttacgccact gaggatcagc ttagaaataa ctggattgca   7680
ggagcaaaaa acgcatggga ggtttacgga caagatgcaa tggatatgta cggcaacgtg   7740
caagatattg caagcgaggc gctcaacggt ctaaccaacc aaatggctac attccttgca   7800
acaggaaagg caaactttaa gagcttcgca acgtcaatca tccaaatgat tatccagatg   7860
atcacgaaga tggttatctt taatgccata tctggtgcga ttggaggtga cacttggacg   7920
attggaagcc ttcttaaaaa tgttggattt gcaactggtg gatacactgg cgacggcggg   7980
aagtatgagc cagcaggtgt tgtccataaa ggcgagtttg tcatgacgaa ggaggcaacg   8040
aagaggatcg gagttggaaa tctttacaaa atgatgcgcg ttatgcaaa tggcggcgtt   8100 gttggcggca cttcatacac tggcggcgga gtttcatctg gagcaacaaa tcttaatatt   8160
ggtgggatta gcgttgatat taacaacgga aacgatccaa aagggttgga gactggcgta   8220
aaaatgattt tcactgatat gattaagcgt tcctgtacgc agggtgggga agtttacgaa   8280
tttgttatgt ctaagcgggg gtgatagtga aacttgagca attcaaatgg tgcacgcaaa   8340
cgcaaggagg cggcggcact atgaccacat caaataacga cagggaaatc tcatttggta   8400
atggttacac gcaggttgcg tcaggagggt ttaacactgt acgcagggag ttttccattg   8460
tctatgtggg taatgattac cgagatgttg ttgacttcct gaatggtcac aggttgaagc   8520 cgttttatg gtttatgcct gacggtcaac ctggtctatt cagggtaaaa tctggtagcg   8580
ttgggttaac tccaatatca gcaaccgttc aggaagtgaa agcaacattt actgagcaat   8640
ttacatcaat gcaataattc aagccgcctt tgtgcggctt ttttattgat gatacaatgt   8700
acgaaaggag gtgcaattat ggctaatgaa acaacaggtc gcgcggatct tgaaaattgt   8760
ctgcaaagcc tttaccctgg cgagattatc acgctaattg agattgacgg tacaaagttt   8820
ggcgcaaaca tttaccgcat acacaatgag aatatatcat acactgcgga agaattatta   8880
caggcgcgag aaactggagt tcttcctccg aaagagatta cattccgtgg cgaggtttac   8940
ggcgcgcgcc cgtttggaat atctggaatc aacttcacaa gcaacggaaa ggctgataag   9000
ccacaattga tactatcaaa ccttgatagc caggtgagcg cgatgattcg caactttaac   9060
ggcatgatgc aagctaaggt tacaatatgg atcacgccag cggaattaat ggggaaagat   9120
ggcagcatta aagatggagc ctcaagaaag ctggtttact acattgagcg accaagccat   9180
tacaatagaa tgatggcgaa atttgacctg acatcgcctt atgatatgga tgggataatg   9240
attcctccgc gaataactca aagcgtttgt tattgggcgc agcgtggatg gtatcgaagc   9300
ggaaaaggtt gcggatacaa tggatcgcga atgtttgaca aagacaacaa tcctgtaacc   9360
gatccatctc aagacttttg cgccggaact gtaacagcgt gcaaacttcg ttttggtgca   9420
gataagcagc ttgattttgg cggcgcacca gtagcaagcc tgttaaggag aaatcagtga   9480
tgattagtgc aaagataaaa cttgaaataa tgcagcacgt aaaagatgaa tacccgcgcg   9540
```

```
aggcgtgcgg ggttatcact caaaagtcgc gggtacagaa atatcaccgc ataacaaacg   9600
tgcatgatga tcctgaaaat cattttgaga tgggcgcaac tgaatacgtt gaggcgtgtg   9660
aaagcggtga gcttattgct gttgtgcata gccacacagg agacggggca agtacaattc   9720
caagcgccca tgacacatgc atgtgtgatg aaatgggtgt ttcatgggtt attgtgtcat   9780
ggcctgaagg tgatatgaga atcattgagc ctgaatctcg tcctctgatt ggtcgcccgt   9840
ggtcgcttgg ggcgtatgat tgctgggggc ttattatggc atggcacaag caacatggcg   9900
ttatcctgaa tgatttcagg aaaccatatg aatggtggaa gcctgagcac ggcgaaaatc   9960
tttaccagga aaattatctg aaagagggtt ttgttgaaac aggagagccg ccaaaacctg  10020
gtgatatggt tatctttcag ctttccgcgc cagtgtggaa tcatgcaggc atttatcttg  10080
gcaacaatca gttgcttcat catgcctttg gtaagttgtc gagggttgat ttgtattctg  10140
gatggtatca ggaacatgca aaaatggttt gtagacataa ggatctgaaa tatgactttg  10200
aaggtaatta aattatctgg atctttaggc cgaagatttg gagtatttca taagctggct  10260
gttgattcat acccagaagc aatacgcgca ctatcttcac aggtggaagg attcaaggac  10320
tacatgcaaa gcgaagtagg atcgcgaatg cgttacgctg tatttgttga cggtaagaat  10380
gtaggacagc acgatgaaaa agcgtggcaa tgtgcaaagg aagtgaggat tattccaatt  10440
ccaacaggtt caaagtctgg cgggttgttt caggttgttc ttggcgcggt tattatggcg  10500
actgcatttt tcactggcgg ctcttcactt gcgttaatgg gtgcttttgc atcgtctgct  10560
tttatgatgg gtggagcaat ggtacttggc ggagtaatgc aaatgatctc accgcagcaa  10620
ggaggatcaa gattgtcatc ccaatcagca gaaaacaagc cgtcttatgc tttcggtggc  10680
gctgttaaca caacggcagc aggatacccc ataccattgc catatggtca aaggaccgtc  10740
ggtggagcta tctggtcggc tgggagttat gcagaagata aggcttaata taaaagagtc  10800
gcgcgttgcg cggcttttttt tttgcccgta taattcaaca aatcaaatag cacaaaaggt  10860
gaaaaagcat ggctgaaaat atgataacgg gcagtaaggg tggatcatca aaaccttatg  10920
tgccaaaaga gatggaagat aacctgatct caatcaacaa aatcaaaatc cttcttgccg  10980
tttccgatgg tgagtgcgat ccagatttta cacttcgcga tctgtatctt gatgatgttc  11040
cggtaattgc agacgacgga actgttaact accagggtgt gaaagctgaa tttcgacctg  11100
gaacgcagac gcaagattac atccaagggt ttactgacac atcaagcgaa gtgacgctgg  11160
cgcgtgacat tacgacgaca aatccttatg taatttccgt aaccaacaaa acattatcgg  11220
ctatcagaat caaaatgcta atgccaacag gcattaagca agaggataac ggcgatcttg  11280
tcggcgttaa ggttacttat gctgttgata tggctgttga cggagactct tacaaagaag  11340
tattgctaga caccatcgaa ggtaaaaacgc gttccggtta cgacagaagc cgaaggattg  11400
accttccggc atttaatgat cgcgtattgc ttagggttag aagggttacg gcagacagcg  11460
catcatctcg cgttactgat ctgattaagc tacaaagtta cgctgaggtt attgatgcaa  11520
aattccgtta tcctctgact ggtcttgtat acgttgaatt tgacagtgag ttgttcccta  11580
accagatccc taacatttca atcaagaaga aatggaagct gattaacgtt ccgagtaact  11640
acgatcctgt tttgagagag tatcatggtt catgggatgg tactttcaag aaagcttggt  11700
cgaacaatcc ggcgtgggtt ctttatgaca ttatcacaaa ccagcgatac ggattagatc  11760
agcgagaact tggtgtgcag gttgacaaat ggagtcttta cgaagcggcg caatactgcg  11820
atcagaaagt gccggatgga aaaggcggta cagagccgcg ttatctatgc gacgttgtga  11880
```

-continued

```
ttcaaagcca gattgaggct tatcagctta ttcgtgatat ttgctcaatc ttccgaggca   11940
tgagcttttg gaatggcgag agcttgtcaa tcgtcattga taagccgcgc gatccgtcgt   12000
acatcttcac caatgacaac gttgttgatg gtgatttca gtacacaaca gcaagcgaaa   12060
agagcatgta cacgcagtgc aacgtgacgt ttgacgacga acaaaacatg tatcaacagg   12120
acgtagaggg cgtattcgac acagaggccg cattgcgctt tggatacaat ccgacaagca   12180
taacagcgat cggatgtaca cgcaggagtg aggctaatcg gcgcggtcga tggatactaa   12240
aaaccaactt gcgcagcact acggtaaact ttgctactgg actggaaggc atgatcccat   12300
caataggtga tgtgattgct attgctgaca actttcacag cagcaacctg aagttaaacc   12360
tgtcagggcg cgtgatggaa gtttccgggt tgcaggtatt cgttccgttt aagattgatg   12420
ctagaccagg tgatttcatt atcatcaaca agccggacgg taagccagtt aagcgcacaa   12480
tctcaaaggt aagcggtgac ggaaaaacca ttgagctaaa cattgggttt gggtttgaag   12540
ttaaacctga cacggttttt gcaatcgacc gcactgatat tgcattgcag caatacgttg   12600
taacgagtat cggcaaaggt gatgatgatg atgaatttac atactccatc acggctgttg   12660
aatatgaccc gaacaaatac gacgagattg attacggagt aaacattgac gacagaccaa   12720
cctcaattgt ccagcctgac acaatggcag caccggaaaa tgtgcaaata tcctcatact   12780
cgcgaattgt ccagggtgca agcgttgaaa caatggttgt gtcgtgggat aaagtacctt   12840
acgcatcgct gtatgaaatg caatggcgaa aaggtgatgg caactggctg aatacaccac   12900
agacagcaaa caaagaaatt gaggttgaag gtatttattc aggaaactac caggtaaggg   12960
ttagatctgt ttctgcttcc ggttcaacgt cgccatggtc cagaattgtg acagcttcac   13020
tgactggtaa ggtaggagag ccaggcgcgc cagttaactt aactgcatca gataatgagg   13080
tgtttggcat tcgtgttaag tggggatgc cagaaggtag cggagacacg gcatacattg   13140
agcttcatca gtcgccagat ggaacggcgg aaaactcaag tctgttaacg ctggtcccat   13200
atccacaata tgaatactgg cacgggacgc ttccggctgg tcatgttgtc tggtatagaa   13260
tccgcagcgt tgacagaatc ggcaacgttt ccggatggac tgattttgtt agaggcatgg   13320
cttcagatga tgtggaggct gttttaggcg atattcttga taagattttt gataccgaag   13380
caggaaagga tctgaaagag aatgccattg atagcgcaaa caaaatcaag gatcaggcac   13440
aaagcatcat tcaaaacgca ttggcgaatg atgcagacgt taggattatg aggaaggaaa   13500
acggaaaacg caaagccgag tttagacaat caatccaatt gatcgcaagt gaaactgagg   13560
cgcgcgttac cgcaatgacg caacttaagg ctgaatttga cgaggaaata actagcgaag   13620
taacgagact cgatcaggca attgcaacag aatcggaaac gcgagcaaca gccattgagg   13680
aattgaaatc acagattggt gatgatattc aggggcaatt aacgcgggtt gaggaagcga   13740
ttgcaaacga acggaggcg cgcgtttcgg ctgatacagc attaacagcg aagtttggag   13800
atgttgaatc agcgcttaca gaaaaacttg attcatgggc tggcgttaat ggagttggcg   13860
cacagtacgc aatgaaactt ggattgacat acaacgggca gaagtacagc gccggaatgg   13920
tcatgcagtt atcaaacagc gctcaagggt tgatttcaca aatcctttt gatgctggaa   13980 gatttgctat catgacgagt tctaccggag ggtcgtatac attgccttt gtggtcgaaa   14040 ataaccaagt tttcattaac agcctgttag tgaaagacgg atcaatcaca aacgccatga   14100
tcggtaactt catccaatca acaattacg tttggaatca aacaggatgg aggcttgata   14160
aaaacggcac gtttgaaaat tatggttcta ctcctggaga gggagccatg aaaatgacaa   14220
acgaaacgat cagccgttagg gatgcaaacg ggcgcttgcg tgttcagatt ggtaggctta   14280
```

```
ctggtacgtg gtaaaatcaa agcggggcat ttgcctcgca tttatggagg tttaataatg    14340
gctgaatatg gtgtttcaac gtgggatgct aacgggaagt ataacaacta cggaatcaag    14400
ccagtttccg ttgttggtgt cattagcctt gccgctggtc agacaagcgg atcgtggagc    14460
tttagcattc caagtggttt taaggttggg tatgttgttt cacttgatga aggtgccagg    14520
ggagttggaa gggaaatagt agcatctgga aacacaataa gaattaatcc tacatcgtca    14580
gttggtgcaa atagatattc ttcttcaaag tgcgagttag ttgtttttct tgagagggct    14640
taaaatggct gaatatggag caatgttatc tttatcaaat gggaatccat ttatcacacc    14700
aaaatcaacg ccatttttgct tatatggcaa gtacacttat tcatcttcag gtacttctgc    14760
ctatcatagc gcaagcgcaa ataccagt aaaccaatct tatccatgca tggcatttat     14820
aaaaacaaca aatacacaac agccaactgc attaatagct tacaggaatg gtggtaatat    14880
ttatgtaaac ggaggaaatc catatggtca atcatttaca atgactgttt atatatttgc    14940
catattccct caaactctac caaaatatgg tatggctata tgggatgcaa gcggcaagtt    15000
agttttaact aatgaaagca gggtgctaac agatcttgtt acaattggta ctcctggttc    15060
ttcaggtgga acgaatatag atcaaacgtt atctggttct tatgccgttt gcccttcaag    15120
gcttggggcg ttataggta tgggcgcttc tgatatatat acatcatgca ggtataatgg     15180
ttcaagcaca aggattggtg cagcaaggac aacgccagga acaggttcta taacaaataa    15240
cggaaattca ataattgcca tcaagactga tatttacgac caataaaaag gggctttcgc    15300
ccctttattt ttatttacag actgcaatca gcgttttta agttgtcaat gcttacccac     15360
tgaaaattaa acgggtagcc agcattaaca agcgtgcgat ttccatctcg ttttactcca    15420
aaaatagcaa ctgaatactg catgccacca ttttcataaa tagccgtgca ttcacgttta    15480
ggcatatttg cgcaaccagt catggcaacg gctgccatca aaatggcgat taactttttc    15540
atcttggtat ctccttcgtt gttgttggtt gcaactatac acgatcttgc ggttggcgtt    15600
tagcaaaaag tgctattctt gttctttttg ttatctggtg ttctcaaatc tgcggagtct    15660
taaatttagc tcaaaaagcg aacaacaata gagcgcaata catacagata aatatataca    15720
tacatataaa tcaataagtt agtagtatat atattcatgt ttgttctta ttgttatcta     15780 tgttttgtgt gattttgtgt gtctggtgat ttttctgtga ttatgcatgt gtcattggtt    15840
atgtgtgtct atatatctat atccggcgca aattgaggaa caagagaaca aaaagacaac    15900
aaagatattt atcaatcact tacatgtaag ttttgttatc caagatagct agaacgttgc    15960
tagaacagaa aaaacaaaat aactattgac taaacgcatc aaatagctac aatgcagaca    16020
taacaaccaa tgagggtaaa tcatgaataa gtttatggcg tacaccagcg aagaaatgag    16080
taatgagctt tatcacgatc cagaagcgtg gactgctgat tatgttagtg gatcaagcct    16140
tgcggagatt tacagcacat gcccggcggc gtggaagttc aagccgcgtg acgataagag    16200
taaggcgcta gttttggta cacagtcgca taccaacttt gaaagcaagg agcttttcga     16260
aaaaacctat cgccgtgcgc cagcgccaga agactttaag gatctgataa ccagccaaac    16320
ggcgcttgct gcaaagctga aatcatttgg cctgaaaggt acaaccggaa agacttaccc    16380
cgaacttata aaaatgatgg ttgactgcgg agaagacctt aacgtcatgt ggttaataga    16440
catgatcgca gaaagccagg ccagggccga tggggttcag ttaatcgagg ctaaagatta    16500
cgattcgtgc gtggcaatgc gccaggttct ggaatcaata ccggaacata acgcatgtat    16560
gaatagcaag acggcacaac gtgaattatc gttgttcggt gaaattaacg gcgtaaaagt    16620
```

```
caaagtgcga tgcgatcacg ttgacgtaac aaagaacgtc accgcaacgc tgattgatgg   16680
ttacgatgaa aaaggtcagc cgatttgccg agatattatt tatccagagg ccattgtgat   16740
cacagactac aaaactacaa tgagcgcgaa tccggctgag tttatgcgcc tggcttacaa   16800
tcacggctat tatttgaaaa tggcgttgca atgtgattta ttcagaaaag cgtatccaga   16860
agaaaagcga cctatagttg tgcgactgtt agcgcaagag aagaaagagc cttatttgcc   16920
gttggctttc cgcatgaata gcgagcaatt gaaaatcggg cgcattcagt atatgagcgt   16980
aattaaccag tttgccatgt gccagcaaca tgacgtttgg ccttcgtatt caaacggcga   17040
gccggaggtt tgccttgata ctcctgattg ggtgcgacgc cagtttaagc aatatcttat   17100
ttaaacagca caaatagcta aacaaatgaa aaatgcggtg ttataattca acgcataagt   17160
taacaacaag cgtgaggaaa taaacatgga aaacaaacaa gtgtcagagg tggcagttca   17220
tatcaacaat tttgcaactg gcatggctat gttgcttcgt gactttgtag cgccacttga   17280
tccaacggca ggcgaagaag aaatggagta catcagaaaa gtaattgatg cggtcgataa   17340
cgtcgtactt gtcgcaacaa tgagcgaaga caacgaggaa gcaatcaagg ctgtaaaaga   17400
aagttctgat cgcatgatgg aaaatctgat taaattacac accgaagaag aaacaaagca   17460
ttaacagcaa taaggcggcg aaagccgcca tgaattacgg gaatcaatca tgaaactatc   17520
agagcaattc gacaaggttt taccagcact gcataaggcg cgcagtttgt ttgtaaaggt   17580
taagaaggat aagcaaaata cacacttaaa aaaccgttac gctacacttg atgccgttct   17640
tgatgcaatc actccagcat tgaacgataa cgagctaatg ttgatgcagg atatgattga   17700
aagcgaacaa cctaacagaa tcaaggttga gacaacagtt cttcatgttt ctggtcagtg   17760
ggtgaaattt tacgcagagc taccaatcgt taaaaacgat cctcaaggtg tcggatctgc   17820
attcacatac gcgcgtcgtt atgcagccgc cgcagcattt ggcttaagcc aggcagacga   17880
tgacgcacag attgccgtta aatctgcaaa cgactggaag cgtgacattg agaaatgcga   17940
aagcgtaaac gaattgcaag aagtgcttaa atcagcatgg aaggcaagcg atccggcaag   18000
caagcaggta attaaagagc attacgagaa gcgcaaggca gagcttgaga tcggcaaagc   18060
acgaggattt aatccagcgc aaccaaagca aaatcttgca tcgccagaag ttgacacaaa   18120
aaacgacgag caagtaaaat cgcaaagtat cactgatttt gaatgattta caggggcgat   18180
tgcgcccctt ttttacagga gaataaaaca tgcatattat tactggtgag atccgaaaag   18240
agccgcgagt aaagcaaatg cctaacggca gcacacttta tgtggttgaa ctttcagagc   18300
gatacaaaga taaagatgga aactggcaat atacaaacta cagtttcttt tttaatgcta   18360
aaacagaagg tcttaagggt tggtatgatg aggcgttcca ggttggcaag gttatttctg   18420
tatcttgcga cacgctgcgc attgaaacgc gtgaatataa cggaaagatg tattcaagtt   18480
taatgccagg aggatttgca aatcttatct tcagtcagcg cggggaaagc cagcaacaat   18540
atcagcagcg aacgcaaggg ggatgggggcc aaccacaaca acagaatcaa ccgcaacaac   18600
cgcaacagcc aagacaaagc aatcaacctc ctatggactt tgatgacgac attcctttct   18660
gatcaacaag ggggcattac gccccttttt cactttcagc catcccaaga acggcaataa   18720
ccttaacagc aattcgcttt gcaagttcgg tttgatgagc gttaagtttt ccagtggtca   18780
ttattgacaa cattccggtc atacttccaa gcccgttaaa atctgacatt gccgatttca   18840
tgattgatat tggtgagtga ccttcatcag ctattgtatg cgctctctct gacaggtctt   18900
taactacctg atctattcct tcactttcg tcatttttctt ttccttcagg agttgattgc   18960
tgttctggca ttacaggcca cgggctaatt gattccctttt ctgctactgg cttttcaggt   19020
```

```
tcaattccta aaaactttcc tacaaactca ccaacaaaat ttgagctatc gcttacataa     19080
acatgcatcc tgtctagatc tgcaacagta acgctatttg gtgcgatcat gatcctctgt     19140
tggtgaaaac cgatatacat cacattagcc ggacgctcaa gagtccccat atttggcgca     19200
attacgccca ttatccaaca ataatgaatg ttgccatcaa gcggctcaca tcctgcgtta     19260
agccagttta ctttctggtg tgggaatgcc attgatgaat cagtagcatc acgccgtaac     19320
gaccatttaa cgccgccaat ctcaatgatt tgtttcggcc tcatcccgtt gaattgagtt     19380
acgccagcgc cattttgatt aatgttttgc atatcggttc accttgttac attgatttca     19440
ttttacgcaa tgcgcagata caagcggcgg caagatcggt taattctttc tctatgccat     19500
gatgcgagcc gtctgccttt tcggtcatta gctctttgta ttccatttct acaatcgaca     19560
ttaagccgcc tggcttgtca atgtgcgcgt cccaggtctt aggatggtgc ttagttcttt     19620
caataacact tcccataact gaatcatgtt tgctatctcg ctcataatca tcatcatgat     19680
catcactccc gattgaaact cgcggcaaat gaatgcgcgg tattttatag ccagcataac     19740
ggatcttcat tatctcgccc tcttgatgaa aagcgccccg aaaggcgctt gatttattat     19800
cagccgcaac agccagtagg cggagtctgc ggagtaggta acttgaagtt caccaattgc     19860
tctacctggt tgattttgca attcagtgcg gcggtctggt ttgcctgaga tagagcaaaa     19920
cgcgcttcct gcaactgagc tttcatatcg caaatcaaaa cagcctgaga atcagcaaac     19980
tgttgacgaa tcagatctcg cgttgcgtta ccttgtcgct caatgttcag gttagtctcg     20040
cagcaacatc tctccgctgc aatctgtgcc tgataggaac gctcaagagc attaacatca     20100
gcagcattaa tcgcagcaac cgtctggtta gtgccgctaa caatcgcggt attcagtccg     20160
gcgaaacctt gcaccgatgc aagcaggttt tgcgtattct ggctggtaat gccgttaaag     20220
gttgatgcgg cggagcgctc aacggcaagg tttgtggagt tttggccttg cagagtttgc     20280
agccccaggt tgtttacgcc tgtctggatg ttattaatac catcaagaac agcgttagca     20340
ccgacagcaa cagcagcgcc atcaccacca tagccaccac gaccattaaa gccgttacca     20400
aaccatgacc caatcaggcc accaacagca ccgccaagac cagccgcgcc agcttcgcca     20460
ccaaaaccac caccagtagg gagtaaagtc atatctgaca tagtaaattc ctctttgacg     20520
ttaaaaaaat taaaaaaagt ttgcaacatt tatgttacga caaagagtat gcgcccaatt     20580
accaggaata gatataaaat atttgtaagc gatatgtaag caactggcat aaagacgaaa     20640
aaagcgcagc atgagccgcg cttgagttaa aaatattgtt atttattgag cagtgcagca     20700
acagccgcct ttaattcgtc tatctccttt tgctggtttt cgatcattcc tcccatgtaa     20760
accatagcgc aagccatatc agccatgatc acgttgttat caagagcaag cgtatcatct     20820
gctttgtcaa ccacaatttg acgatctaca tattcttcac cttcatcatt aacgcctata     20880
acatctgcaa aaatgtcccc gccaggtatt agctttacat attcaggatc tattttagc      20940 agatcctggg ctatcatccc gaatcgctgg atgttgcttc cattgtattt aaacattgtc     21000
ggaagccact gcataacgcg atcatagctt tcttttccat ctgtataaat tatgtcgtgc     21060
tttaaatctc tgtcagagtt agcggccttt tgaaaaatga aatttccact tgatgaccat     21120
gtggttatat cgtttgaggc tggctgaaac tggaagttac agaaaaaact accatcacca     21180
cgaagtctta acgagcaaaa aggccaagcg ttattgcctt gtgggataag accccatgtt     21240
gcgcgaattg gataaccacc tgttgattga gtacccccatg atagacctgg cgcccatcca     21300
ccatcattgt taggaataat ctcgccccaa acaagagcat taccccaata gttaggatca     21360
```

```
tcccagccca tttgctgggt tttgccagtg tattgagcag aatgcgttct gccgtcaggg    21420
taaaacttgt gcatatagct ttgcacgcca tgtttataca gttcaatccc aaacgactca    21480
atttgtgcag caccgcctct gatcaaacca gcgatagcgt aatcgttata ccagttgtaa    21540
cgacttacac cagtccatga gttcattggt ggattcatga ttgaatatag ttgtgacgga    21600
ttgtgttcat tcccgtctac ataaatacca gccccaggag ctaaggcaat acttttcgct    21660
cctgaaaaag caccattttc attaaactga taatactgtg ataacccatt atgaaatacg    21720
cctattgtat gctttcctac gcctacttga gtctcaaaat aagactgaga agacccaata    21780
tcttcgcctt gtgtactctt taattttgaa tggtatatac ctgcgtttgc agtagctgca    21840
tttccagttt cattttcaac attaaggctt aggaattttg gtgcatgttt ttcgccaagt    21900
cctatattgt ttctgatgcc atttgcgtca atagctccag taccaccaga gaaatagct    21960 aaaggcacag tttcaaatgc accagatcca gaaatatctc tctgaaaaac aagaagacca    22020
tcatttctga taacaagcct atattctcta tttctagagt acaagatagt atgtacgtaa    22080
tcctgaaaaa atgaatcaat actaagcgtc tggcgagcag attcaatgtc agaaagatct    22140
ttaagattct gatccttatg taatatattt tcaggattta cctgttgcgc ccactgtcga    22200
gcttcatcac gcgcagtttc agcgccagcc tttgcattat ttgcatcaac ggcatgattt    22260
ccagcagcat cacgcgccaa tacagcctga tcgcgagcgc cgaaagcatc ttgtttaatg    22320
gcttccgttt cgattatagc tgaatcttta atctgttgcg tttgcgcctt gattgcgtca    22380
gtgtctgatt taatctggtt tgtttcagca acagcagaat cctttatctg ttgagtgttg    22440
tttttcagtt gttcagtagc agcgcgatca ttggccgttt tctctgcatc acttttaacc    22500
tgattagcca gatcttgcag ctgctttagg tcaaagtttt tgaaaaattc aatagcttcc    22560
tcgatctgag tttctttgct ttgatagtaa cgcagcgttt ccgcaacatc ttgtgctagg    22620
ccgtcaacag tgattgagtc atgcagcaaa ataatgtagt tgcttcgccc aatttcagcg    22680
ccgccagttg tgatggcgcg aatttgtgta tcgctgataa cttcactgat cacggccgct    22740
tgaaatggag catcaatgaa aaagattgtt gcaccagggc gaatgagcgt tagttgctct    22800 cgccatttg tgtcgtatcc agtgatataa ccttgcgcgt ccattgacgc ttgtcctgtt    22860
ctgtaaattg ccatgcgttt tctcccgtgt tgcatgttaa tgtcaatgca gataatagca    22920
tttgctaagg aaaaaaaaaa ccccgcaatg cggggtaaaa gtagcagtga catttagaga    22980
agagattcag gtttgtaaac cttcctctct atcccttgcc tgtaattatc atgaatcggc    23040
atcataattt caagtcctct ttcctcggca gcaatgatcg cgtcacggtc tgtactctta    23100
cagacaactc gcattcttct gttgccttta tacctgtaag ctacaatttc aatgttagtt    23160
gcatcaaagc aggcccaaac ctcctgacca gttgcaaggt gaatatgttg cgcatcaatc    23220
cagtcaacgc aaagatagat cgtcttatct gtgcttcctg ttctaacaac cgaccccgc    23280 gtgtagtcct ttgcgagaaa agacttatta ccttcttcat caatgaaaag cacattgcac    23340
atttcatcat caatttcatc tgaatgtacc aggtaacatg ggagcgcgtg aatgtatcga    23400
ccatctttaa cgccgcaatc ataatgacca tcttcaggcg ggtatattcc ttcatatgtg    23460
cttaacggcg tgcgatcaaa ttttagtgtt tttgacataa cgcgctcgca gcattcatgg    23520
cttgcctgtt tcccaaacga ataaccagaa tcacgagata ctcgcttatt tgccttgatt    23580
ctatagtcct gcggaacttt tccaagaaaa cggcccaaaa tattgatcac ttcgctgtaa    23640
ggttctccgg ttagcttcat gatccaacca attccggtat cattaccgca cacgttgcag    23700
atcgcaccgc catcgccttt tttatcgcca agtttatccg tccatctgaa gcgatccttt    23760
```

```
ccgccgcagt gggggcaaga ttgatgcttg ccgttaaaaa cttcatttgg aagaccgcaa    23820
atactttgta gcgcctcacg ccacaatcct tgcatatatg ggagaacatc ttccttttga    23880
taaaccataa agttttcgtt gttcatatgc acctcaaaca aaaagcctga cagatgataa    23940
catcatgcca ggcattgttt ttagcaatta gtgctttcag gtttatacag gaatccgcca    24000
ggttcataat ctgacattct taccactcgc aacatttcac gcttatcaca tctctttgtg    24060
agcggttttc cattggaatc aaatcgcaga tctggacggc agaatgaagc gcgatatcct    24120
tgacagccat acttttttgta atcgttatgc accttttgag cgccagctgc tgaaatcata    24180
ccgcgaactc gccactgatt tacagtttgc tggctaacgt taagacgttt tgccattgct    24240
gacacgctgc cgtaatactc aataagaata tcaagccgtg cttttagtcc ggcgcgcact    24300
tcatctttta gaacataata acctgtcggt cgcttgcgct tcttcttgtc cttgcctcgt    24360
cttgttccgt tattgccatt aattgtgcgt ttgtcaatct taccagttga tactgcgatt    24420
cgctgttctt tcattattca ttctccaata gcatttttttg ttaaacgatg atttaatgat    24480
tgtgtattat acacgccaaa tggcattact caaaggtttt agaatgattc caaacattga    24540
aaagcaaata tcagcacttg gtgaagcggt aattaaatcc attcaggagc gattcactgt    24600
tggagagatt gtgccttacc cttaccagtg cgttgcatac gctgagatcg caaagcgtat    24660
gaaaaattat gagcatccat tctttgttaa agcgtccgta tcggctggca aaacattgat    24720
gtttgcaatg gttgctcacc agtgccggaa aatgggcttg aaaatgatgg tccttgctcg    24780
acaggctgag attgtggatc aggattctga agagataaca aatcttggtg tgccgaactc    24840
catctattgt gcaggactga agacaaaaag cgcatacttt ccgatcgttg ttggttctga    24900
gggaactgta gttaatggac tgtttaaagc gcttggcgac tatgttccgc acgttatcgg    24960
gatcgacgag tgtcaccagg tggattggga agaccttgcc gacgcaatag agaaagacga    25020
gtcattttta caaatgacaa ctaagaaagg cgaaaaagta ccaaatccag attatgacat    25080
aacaaaggga agcaggaaca gaaatacaga gttcctgatt ggtgaggatg gcttgccaat    25140
ggagggaaca ggccgcacac aatacactgt cattatcatg gaaatgatgc gccgctgccg    25200
gaaaacatat ggtcatgaac tgcgcatatt tggcatgact ggatcggagt ttcgcggcgt    25260
agtcccgatc ctggtagaag acaaaaaaca gaaaggattc tggcgtgaac aggttactaa    25320
tattgacacc aactacctga tcaaattcgg ttctgttgtg ccaacaaatt ttggcgacgt    25380
tggcgatcta gggtatgacc tttcagagtt tgaggcatcc agtgaggatg gcgttgcaga    25440
ctttgatgct aaaacgcttc gcaggatgga acaaaaaatt catgaagaag cgaccatgac    25500
aaagcgcatc atggcgaaag ttcacgagat ctgtaaaaac cgcaacggcg tacttgtgac    25560
atgtgcagga gaaaggcatt gcaaagaggc agcggcagca ttgccacctg gaacgactta    25620
caggatcatt actggtaaga ctggcgacaa tcagcgcaag gagtggttga aggaagcata    25680
cgaagggaag gtaaaataca tattccaggt tcaggcgcta actactggcg ttaacgtgcc    25740
gttttgggat acgtctgtta ttctgcgtaa gattggatcg ctaactttgc tgattcagct    25800
tttaggacgc ggaatgcgac ttcttaagaa atggcataag gagcaaggct tcaagaaaga    25860
tgatcacctg gttatggatt tttcaggaac gatggacgag ttaggtgagc tttatttttga    25920 tccgatactg gaacaggcgc aacatcagaa gcgattcagg aacggtaaag atccgaagcc    25980
ttgtcctgtt tgcggaactc ttaatagcta ttatgctcgt cgttgtatgc acgtagacga    26040
aaacggcaac agatgcgagt ggttctttaa attcaggaca tgtgatgatc agattgaccc    26100
```

```
gcgcactaaa aagattattc agcgcggttg tggaacgaag aatgatattg cggccagggt    26160
atgcagacat tgcgacatgt cattgattga ccctaacgag aagttaagcg aaaagcacta    26220
cacaaaaaac gactggttcc aggtgcaatc tttctcggtt gacatgacga aaaaccagaa    26280
agggataata tttaattatg agctttccga tggcatagac actttcaggg cgagagagat    26340 attttttccct gaatctgaga gccaaatttg ccgcgcaaaa tggcgaagcg ttgctcttaa    26400
gcacatacca gatcgccgtg tcgctggcat ggtggcgagc tatcgtaatg cacgtaaaat    26460
catgcaatat gtgaatcaca tcatgccacc atcgcgtgta actcaccgca agactagcaa    26520
gggtgaagat aatttgtaca agaaggactt taattatggc aatgactgat aaaggcgatt    26580
atctggagtt ttacgaaaga gatccgacgg atacgctaaa ggaggagtca caccagatcg    26640
gggcgtttca atggttaact tatgctcatc ctgaatttct tgcctggcat actaaaaatg    26700
agggcgacaa ggggatcgcc accgcaatga tggatcagca agccggacta gttaagggcg    26760
taagtgattt catcatcctg attggattaa aaggccgcta tccttttgca gcaattgaga    26820
tgaagcgcgt caataagtca ggcaagggga aggcttcacc agtcagcaag gagcaaaaag    26880
ccttcttgcg ccgtgtgcgt gagcttggcg gattcgctgc cgtaacatac ggatataagc    26940
aattcatgat cgcggtagaa tacatgatga atagcacttt tttgttaaaa caggcgcgaa    27000
ggattgcgcc ataataacac cagttcaaca agcaacaggt aattaagaaa tgagtaaaga    27060
aactgaagtg acatttgaac aaatagaacg cgaaacattc attggcaatg ctcttgctac    27120
tggaggccat taccaagccg ttaaaccaaa tcaatattat aaagtcactg caaccgcta    27180 taacggcagc aatacgccgg acattgtgcg cgatttgtgg tctacgccgt atgagcttgt    27240
agcatggatg gaaagcgaat acggtgatta tgacatcgac gcggcggcaa gcaaagaaaa    27300
tgctgtatgt gaaaaattct acagcaagga acaaattgc ttaaagcgtt ggtggggtag    27360
taacaagcat atatggctga atccgccgta cagcaatata cgcctttcg ttaagaaagc    27420 gattgagcaa atggagcaca ataaccagat cgacattctg ttaccttgcg acacatcgac    27480
aggatggttt tatgaggcac aacagaaagc agcggaaatc atctggatca ctggcgaagt    27540
ttaccaggag gacggaacag aatattcccg cactggacgc ctggcgttca cttcagcgct    27600
tacaggtaaa ccagttcagg gaaacaacaa aggcagcgtt atttttcatca tgcgcgaact    27660 taaagaaggt gagcagcaga aaacgcgata cgttaaaatc agcgacattt gcccgtcagt    27720
ggcagagcgt cgcgcacgca aacggagcta aaaccatgca gaaagaaaga agagttttac    27780
ttaatgaaga tggcgaattt cttttgtatc gcgctatggt atgcgatgca cttgataaaa    27840
accctaacgt gaaaaagatg attgattgcg atccgtggga attttcaagc tcattagata    27900
tgagctttga ggagacaaaa aaactcccac ttgaaaaatg gcacgaacaa atcagaaatg    27960
acatgcaaga atttgtcgat tcgtggaatt ttcataacgg aatgatccac caatagcact    28020
ttttgttaaa acgcccggcc ttgtgtcggg cataattatt tcatcaaaac gaacaagagg    28080
aaaacaaaat ggttgtttac gatccacgcg cttttaaaat tgctcaagaa gtttcacgcg    28140
aatctgttgc tggtggttcg gttaacggct atcagtttga ttggtcggca gcaatgaccc    28200
tgcttaaggt tgcatatggt cacgcgccaa ttgaaacagc ggaggaatat tataagcatg    28260
aaggttgaac aaggtaggca ggccgtatgg gatcacgcaa aggagtgcgg gatctctgaa    28320
gacatagcca ggatagcaaa atattttgat attgctgaca taagcattat cagcggcgac    28380 aaaatgcat ttctcaatga acgaccgcgc aagatgcatc gcgtaccagc aataccaaca    28440
aagattgatt tcaaagaggc tatggcgaaa attcgcgagc cgcgcaaata ctacaaatga    28500
```

```
ggattattat catgtggcgt ttgttacttt tgcccttacc tgttatgatg gcgatctcta    28560
ttgtatacgt tgtcataatg agataaggag aattttgat gaagcaaatc aaaatcacag    28620
atgaacaatt tatcaatgag cgcaagcagg gaaagacata taagcagatc gctaatgagt    28680
atggtatgaa cgttcgcagc attgagcgac gcgcggcacg attagcaaag caaggtaaag    28740
ttacaaccat cggatcacct ggttttggtg ttactggaga atcaaagcta attgataaag    28800
atggcaatgt ggttatgaca tggattaaga caagtaagga ccgcgaacag ttagaagcat    28860
taatgcaggc cgctatggat gcatttagcg aagaagttcc tcgacttgat ccacagccag    28920
aatcacaaaa ggattatagc gagacgttat cactgtatcc gatctttgac atgcacttgg    28980
gagcaatggc gcataagcat gaatgcggcg agaattggga tacagcaaca gcagagcgcg    29040
taatgaataa ttttattgat tattccatcc agtgcgcgcc ggatagtgaa aaagctgttt    29100
tgctgattgg cggtgatatg cttcacagcg acggactgga agcggtgaca cctgcaagcg    29160
gtcacgtatt agatcaagat agtcgatacg caaaacttgt ttatgttgcc atccggtcag    29220
tgcgtcgagc aatcacaaag ctgttatcaa acacaaaaa cgtcgagatt cagattattg    29280
aaggaaacca cgaccaaagc ggcatgatct ggttgcgcgc agcaatggcg gcagcatatg    29340
agaatgagcc acgagtgcat gttgatgtat ctccgcgagt agttcatcac acacaatatg    29400
gcaaaacatt cctggcatac catcacgggc atactatccg caaacctgaa acattgctca    29460
tgatgtgcgc ggcagactgg cgcgaagact tcggcaattc aaaaatgatg tatgctcacg    29520
tagggcattg gcatcatcaa acagtaaccg aaacaagcct gggcattgtt gaagtgcata    29580
gcactatggc ggcaaaagat gcatatgctg cgcgcggtgg atggcgttct cgtcgccgtg    29640
cggctgttat tgtttacgat aaagaatacg gagaagtagg gcgatttatg cattatccag    29700
aaatggctgg ttgaactttt aatcattaaa atataaatat aaatcatcaa tttaattggg    29760
cgtggcattt tgcttcgccc ttttttatt ccttttgtg cgttcaatgg ttaggataca    29820
atcaattaat tgttgacttt tatctacagg agatctaatc atgaaagatt ttttaaacgc    29880
tgcaacttcc ggcactggcg gcgcgtcaat cactggcgca gtaactggtc aaacaactat    29940
cgcaatagcc agcttagttt tgatggctgc atttggcatg tggggcgctt atcttcgttg    30000
gcgtgatagt aaggcgctac gtgatgcgct tgaatgcggt gatattaaga aagctattga    30060
gatcagaggg aaataatgag tataaaacaa agagtgaccg ctgcggcttt tggcgttgct    30120
cttgccctta cttctccgct actggaggaa atagaaggag taaaacataa gccgtacaaa    30180
gatattgctg gatatggac ggtttgcgcc ggaataactg gacctgacgt aatacaaggc    30240
aaaacgtaca cacaaagaga gtgcgatgca ctactggcaa agcatatcaa gatcgcaaag    30300
gatgaagtta taagcgtgt aaaggttgac attcctgata caatgcgcgc agcaatgtat    30360
tcattcacat acaatgctgg aactggagct tttagaaatt caaccatgct taagctgatt    30420
aatagcggtc gttacatgga agcgtgcaat cagttatggc gatggacaaa atacaccaat    30480
ccaaaaacag gaaagaaaga aacgtctaaa ggactgcgca accgccgcgc ggtggaattt    30540
aaatattgca ttaaggatct gtaatcatga gaaagttatc agcaatcgcg atcgctgtta    30600
ttttgtctgg atgttcaagc gttacgccgc tgaccggatt aatcggtagt aagccggaaa    30660
tcacagcaca ggcaggagcg gagaacgtaa agcagaacgt tggcgttacc gcaaagcagg    30720
acaccagcac aaaacaggaa actacaataa aggaatctgc ggttgataag gtggacactt    30780
ccagcaagaa ggatttcact acgtcaacca ttcaggcaaa caccataaag gctgataaaa    30840
```

```
tccaggttgt gcagggtaat aacggcagat ggtacgaccc cataataata tgcgtggtag   30900
tgttccttgt gctgatttgt ctttactgga gggaaaagaa aaaggaggct taacgcctcc   30960
tttgttttat agtgaatcca tcaaatcttg aaagctgttt ccgctataat cattctcgac   31020
aagaatgtaa gcacctttct tctttatatc ccataacatt tcattgtatt cgtaacgatt   31080
tatttcaaac gtgctgccat cttctcttgt cgcagttcct ttgtcgttga aaacatcaaa   31140
agttacattg atgattttg tctctttctt tgttactttg atagccattt ttaaaatcct    31200
catattcgtt tcgatgaaac aaatataccc gattcgagat cgggagtttt aacaaaaagt   31260
gctattcaat acgctttaca gtaaccaaca aaacgccgtc ctcatcacac aaattatgct   31320
ctgatatgtt aaacgctcgc atgtcagaat gaattagcgt taacattgcg tgcatgaaat   31380
cgtcatgtga gattgaactt acggcgcaga acttcaatat tttgtctatt agcatttgac   31440
gtaaacaatt cttcatcgct catttctccg atccttaaaa catcccttac ccattcgttt   31500
tgcatacctt ccaggctgta aagttcaaac gagaaggggc gatttgctga tcctttctta   31560
caccagaact ttccaccaac tccatcaaga taaccagtgg tcatcattct tgcgcaaaac   31620
tcttttgaaa cggcggttgc aaacattctc ggcgtaaatc ctgcgaccct tgcgagccgc   31680
tcacattctc tatgctgaaa tataaatttt gctatatgtt gacgtgtaaa ccattcgaat   31740
gactcacacc agcgatacag atccagaaga aacataatta ccccagcaat gttggattca   31800
cgaaaacaac gccattaatc acacaaatat aatttctttc ctcaagcata ggaagcagtt   31860
gcgtttccat gcgcttcatt acgccagcct gaccaacaaa cggcttaact tttcgtgcag   31920
cctcatatat ggcgcgcaca ttcaagatcc ccttgttagc cttaccgtgt cgagtgataa   31980
tctcgattag tttacccatt tcagcatcat caccagcata gccagaagcg ttggcggcgc   32040
taatgtatgt tttgctcaac tcgctaaaca tcaacagtgc ttcctgaacg gtttcaacct   32100
caatctcttt cgactttga gggtatccgc caggattaaa ccaattgcgg atagtgtgca    32160
aaaccgaagc aatcctgatc acctgcttat ccattttgcc aagagcaccg cgcagcattg   32220
tatgcgaata cttccgcca tcagcaaggt gcggctccat ctcctgacga gccatgttaa    32280
gaactcgcat tgctgatttg ctgatcttaa gctggatgtt tgattcactc atgatgttat   32340
ggatcagctt gaaatattgg cttttcagtt ccccatcaac aggctcataa gtagaatcac   32400
cgttatcatc aacaaacttt ctacgaccta aaaatgattc ctcacgcaca agcaaataac   32460
gctcacttac accgataccg cgcgatcctg catccatgat ggcattgatt gtttcatcct   32520
gggcaattac cgcccatacag ccaagagctt taaaactcat attgttgtca gcgtttgcac  32580
gagctataga aacatgaccg tgatcccatg cttttaatac aagttcgctg ttggttttac   32640
gttcgctatt ggcatatgtc agacctaaaa ggctgttaat acttgttgcc tcgtctgaaa   32700
tcacagcaaa gttaccctgg cgattgttga ttcttgcaag tccttccggc gttgtgtcgg   32760
acacagggaa aacgatgtca cacatctttt ccagttttc ttccagatct tctttctcct    32820
ggtacagaga ttccatatca gcgccggagc gctcgctttt catctctttt gcaagacctg   32880
ccaactttgc ctgaatcttt tttcttttcct tctttcgctg atcattaatt ctttccactt   32940
cagcaaccat aggagcaagt gccaggctgt taacggcaga tttaccagtt gatggaggct   33000
ggcttgtgac aacgtaaaga gcggttggtt gatccgttcc gtgatactca accgtgaagc   33060
gtccaagcat tgcagcagac acgcagccga taaaatgcat atatgccgat gattcaggga   33120
actgaactga tcgagcaatg ttgcgcgcca acttaccaac aacatcaaca tcattgccaa   33180
gagaaattac agggtagcga tcgtttccgt tattaacatc attaacctca ccccaaaagc   33240
```

```
tggacgattg acggtatccg tttgcctgaa tggacacgcg caccggagac aatccttgtg    33300
catcagctaa ttcgataatt tgttttggtg ttagtttatt ggtttcaaac gaaaaattca    33360
ttgatgataa ctccttttt gatgcggcaa taataccgca ccaatgctac ccgcatttaa    33420
caaaaaatgc tatttgatcc gctctatgct aactaagatt ttttctggtt cccttgcgct    33480
atagcaatgc gcggttacgg aatcagcaaa atcaaagtaa agtgatttgt ggtaagaaag    33540
accaatcagc catccaacca tcgttttctt tattggcctg actatatcgc caggcttgaa    33600 ggttttttgtt gccgaatgag tcaccttata gcgatattca gccttgatca cttatacata    33660
gcctcaaaca aatgacagcc accagcggaa aatccaactt cttcgcggta tagcgtccag    33720
cggtcgccag attcatcaaa acataacca gcaacagcgc caagcgcgcg gccttgctca    33780
atctggtagc gcttcccttc tttgaaatgc ttttttacacg ggatcttgtg atctacaaag    33840
gtgcatttaa tcgtttttgt cttgatatga cgatagtcag actcaacagc gttttgccac    33900
ttgctaccct ttgtaatgct ctttacctga aattgttcca actcgatcac atcatcgcta    33960
ccagcaattt tttcgtatac agctttataa cgacagttca tcaaaacgtt ggttttattg    34020
cagataactt tcatcgttta tttctccttt cgtttcggtg aagtgattat gccaggcttt    34080
tacacctggc ttttaacaaa aagtgctatt ttgcgtttgc ttcaaagacg gcgcgagcaa    34140
aacctcgcgg agtgagggag cggatcatct ttgtgcgaga tgattttccg ccagttttgg    34200
cccaaccagg attatccttg tcatcctctt taggaaggat tgttgcgcgc ggaggaataa    34260
caaatccgtt tccagtccaa aggcatgttt tcttaaagta ccgatcccgc gccggaataa    34320
tatcagggaa gtcgggatgc ttatcatctt ccggcagata gccagcataa tcgcacggat    34380
ggaacgtata atcaggcttg cgccataacg ttgacagctt gcctacagga ttctctatca    34440
tgtacggaac accgaaataa tcagcgatat gcgccgcaat tttgcaagtg tcggcggctt    34500
catattggaa gttaggattt tccatgcgct ttttagccca atgacgagat ccgctatttg    34560
ctaattgtgt gcaaggcgga aatgccataa tgaaatcagg cttaccccaa ttttcaagtt    34620
ttgcggtata tttgaatagc tcatcaatcc acacattaac gtaaaaaata ttgtcgtgga    34680
ttatgcgcac tgattggtaa tcgccatgat ctgcatcatc gtaattaaag caaatgcatt    34740
tatatccagc atcagcccaa tctttaacgg ccttaccaga tccatcaaac aaagagaata    34800 ttaaacctt tatcatttca tcacctcaaa acggaaagca tctaggacag ttaggatcaa    34860
aattgcaacc acaatcatta acaatcatag ttggatctgc aaatgcagcg ccgcattcat    34920
ggtccatatc catttcaccc aacgcatcat caagcgtcct gatttatat gcgacttcaa    34980 gcgcggcctc tttattcagt ccggcatctt ctgcttttg cagtcgctca aaaaacccgt    35040
cttgactcat ttaataaact ccttaataac agcaataata attacaagcc cagcagtaaa    35100
aacaagcaat ccgacaaggc caatcataac accaaataaa atatcaagca tcttaatcat    35160
ttattcacca ttgataaaac gggaggcggc aacctcccat tgattaatca tacagccttc    35220
cagctttcaa taaacatgct gttttcttcc agcagtttaa tcaattcttc gcgtgtatat    35280
ttgcggattt tactacctgg atgtgagcca acaacaaaca caccttttacc actcgtgatg    35340 gttaactggt tgattccgca agatttatcc atcttaatgg cgacgcggtg atgtgcatca    35400
acagtgtgca tgatgttagt gactttagct ttcattatgc gatcctcatt gcacttagtg    35460
tagggcatta tatttacttc aaattctcga tcttgttctt tccaattgag ttgtgaacgc    35520
gatgttcttg cgtctctta tctccatgaa catcaatata ataaccaggt atggcagtga    35580
```

```
aaaaccaatt tccacgccag aaaaaataaa ggccgtgatt gcttcctttc gcgcatttgt  35640
ttgcattttt aggtattgga agtccgtgta ctctccgcaa ttctacattc ttgttaaaat  35700
ttggcattac acaacctcca taaaagtatt gaatccacgc agtttgaaag cattgccatg  35760
tttaacaacg ttccatgtca ggccggagtg atacgcaacc atatcctcaa gatcaatggt  35820
gatgacagtg cctttcttaa agattccttt ctcgtgagtg ttgtcacgct gtacaacttt  35880
aacatcaact tgattttcca tttttaaatc ctcgttcgtt gtcgatgcgc ttaatatacc  35940
aatcagcagc gcatcggttt taacaaaaag tgctattcaa caacagatcc agttaaagag  36000
ataagctgcc ttgtgatctt gtgtctgcga tactggcgcg caacaaccgg aagattttca  36060
ccgctttgat gaccgaagca gatcggcaac tcaccctcaa gagagcggaa gccgccaaat  36120
tcaagatccc gcactggctt tgagcgccac gcttcaataa atccgcgttc gtcacgcgtg  36180
atatagcggt atatgttagg gagggcaatt tgtatcccct caaaatccac agtatcggta  36240
tagctgtaaa acttagaact catagtcaac aaccccaaat tcgttaacaa tttgcgcctt  36300
atagaagccg ccattttcg ccaggttgta gcaggccgct acagtttcaa attcgcgcgc  36360
ttccggctgg ctgttttcgt gttcccaggt aatcagagta accattttca aatcctcgca  36420
ttcgttgtcg atgtgtgtaa tatatcggat tgcgaggatt gagttttaac aaaaagtgct  36480
atttagtcca ggagttcgat ttcgcgctcg ccagttaacg gatctttaat ccagaatcca  36540
agcgcctcac cgtaaatacc gccatagaat ccaagcgccg acagatcctc acctttaaca  36600
aataccagat ccccgctacg gcttacgtga gatacgttaa cgataaccgg aaaggtgcga  36660
tccttaaatg caggccgcag agcgtaacac ccgttattga gcaaacgtgc tttgcgctta  36720
actggaatag gtgcattgat tcgcgccatc tttatttctc cttcattgtt gatcgtgttt  36780
aacggccatc agaacatcac aggactcgtt aatgaattta gccatgcgtt tatcatcacc  36840
aacagggatt agcgcgttaa actcgcgttt gctactgaat accgtcactt tatgaaacga  36900
tgcgaacggc atcgacggga actcgactgt ttgcatcaag atccgcaatc ccatcttttt  36960
ggcccttacc tgggcctcgg caagttcaaa atccacttcg ctaatcattt cttgatctcc  37020
tcagcaataa acttcaggac tttgcgcaaa aacacttcat tattgatggt cgctggcaat  37080
tcctctttca cttcttgcgg cagatagata ttgccgtgcc aggtcaaaca atcgtagttg  37140
atacgataag agcaaagcca ctcgcaatcg ttatctgctt cccaaatgca gagttgcaga  37200
acatcgccaa aattctcaac agtcaggtcc agaccatgac gcttggcgaa gttaaaagtg  37260
gttttgctga tgttcatttg cttctcctg atgggtatct cgtttcgatg tgtgtaatgt  37320
acccgatcag gatgattcag ttttaacaaa aagtgctatt tctcaactgg cgattattcc  37380
agctattcca ttaatcagga ataacaagaa taactcattc gcgatcacct ggattgtgag  37440
actttgagtt tgatcaattt taatcaagtg attaactttt tgtgtggagg ggatagagaa  37500
acgcggtcct cttgcatcct ttccggcaat cctggcgcgc aacatgttca ttatgtttcc  37560
agccgttcac gcaaataagc ctccgcagtt cttacacgtt tcatgatgtc atgcacacaa  37620
aagaaacaaa gtaaaatcta tataaataca cattaaatca ataagttagt tatatatgta  37680
tttatatttg tttcttattg ttcttgttgt gtgatggtta ttggtgtatg ttgcgatttt  37740
tgttttggtg gatattgatt gtttattgtt cgatttggtt ggtgatcatg attgctcatg  37800
gttgcgtatg attcttgatg tatttatgta tatatccgcg aaaattcgtg aacagccaca  37860
cagccaaaaa acatggcgag gattctttg aaatcatgtg cttaagtgtg aattttgttt  37920
ccgcgcaatc tccacacgta tagcaaacaa ttagaacgct tgacatagac acggcgcggt  37980
```

```
ggcaacattg caatcaccaa caaacaaggc aaataggagt tacactcatg actatgacaa  38040
gtaaagaatt ttgcgatatg ttgcgagtta atgcagcctc actagctaac ggggatgtta  38100
gcgaactgca aatcaaggag cttgacttac aatgtaatat tgcgccggaa gacttgagga  38160
aaattaacgc ctcatacatc agaacgatta tgaatcgaac gccggagtg aaagctgttg   38220 gcgcggtgaa ggttgagcgc gttcgaggtg atgcggatat tcctgattgc tatcgcgtaa  38280
ccattaacca gaatccaaag cgccgcttgc tgacagatga agatctgcca aaacttgaaa  38340
gtaagtggcg agcaaagttt attgctcaac tactgaaaac acagccgcga atcagtgatc  38400
tggaaggtga gcgcctggaa ggtgcagcaa tcgcacttga gcgaatgaat gaaatgctca  38460
acgagatggt aaaggtgggg gatgaataat gaataaggca ttaattggag ttttgattgc  38520
aattgccacc ctgaccggat gcgaaaaggc atctgaatca acgttgtcg taggagtgga   38580 gtcagatttc aaagtcggtc gcctgtttac tgttgatgga tgcactgcgt accgattcta  38640
tgacaacggt cgcgcgatct attacaccaa ttgtaatggc gcaactgata gcacataccg  38700
cagcggcaaa aacgtaatgc accaacaagt cacaacagat attaaatagc acttttgtt   38760 aaaactcaaa aacgataacc aggcataata gcctcatcga aacgagattg aggaaaacaa  38820
aatggcacgt cgcatcacca aagaccttaa agtcctgaat aaagaaaacg tagttaaaat  38880
cctggttatc tggggctaca cgaagaaac agcaaagcag aaggtagagg caggttatga   38940
cctggctgta aaagcaatgc caaacgacga cgccaaaggc attgcaaact atgtagcttt  39000
cttttaatta gcaggtgaat aaatgaaaac gaaattagtc cataaatcag aaatcaagat  39060
cggcgacact gtgattcaca acagcgagct tagaacggtt ggcaaagagt caatacgcca  39120
cgatgaattt atgggatct tgttgttcgg tgactcttat cggcttggct ataaaatggt   39180
tgagcttgtg gaagaggtaa aattctaaat agcacttttt gttaaaactc aaaaacgata  39240
accaggcata atacatcaca tagggcggca cggcgtcgcc cagttaaacc aatcaggaga  39300
aagtaccatg ttaaaattgg ctgacatcaa attcccgatc accttcgaat ctcgcggaat  39360
tggccattac acgttcacag ataagaacac ttgtcataag ttttggtcgc atagcgacaa  39420
gccagagtta tcaactatgg aaattgagca cttcattgat gcgcataata gcctttatgt  39480
gaaaacgaag gactatggct acgcaatgcc aggatacact tgtttgcact acaaaccata  39540
taaaggccaa gtgttaccag tgcgctcaac tgagcgatca gagattcata cggtcgagat  39600
gaaaacctgc gactacaaaa agctgtggtg cttaagtgtg gacaatatca gtatccgat   39660 cacgttctac acggttggta attcaacgat tcgcttcaca tcgcgcgaca atggcgttta  39720
tagcgatggt cagaaatcgg agttgaaagt tgatttcttt gttaatggtc acaacaaatt  39780
caatccgcac aatgaaaagg ataaggtgta ctacgtggaa gatattacaa acacttgtt   39840 tggagaaaca ccattcggcg gcggaaagac gtcaattcaa caaatcattg gcgaggagat  39900
ccacaaggca gccgttaaaa tgaaagcgcc tggaggctgg cgtattgaca gagcggctt   39960 tgccaatcaa gaaatcgtaa cgcagggcga aatcgaagac atgccgctcg gcgcttcaat  40020
catcggcatc agagacaata acggcgactg gaatgatgtt tcattccctg tcaagcggat  40080
cgagttgcac gaagacatga tttgcatcat ggcgcatcat ggtagctata aggacaaacc  40140
attcgccgca gagcttaaca tcaaacgcgg aacgattgtt aagtggaagt ttaaagtgta  40200
aatagcacga attgttaaaa ctcaaatgtg gggccaagta taatggcctc actttcaacg  40260
aaggggataa aacgatgtac attagcaaga agatgaaatg cgtttccgtt aattatggtt  40320
```

```
gtgctggaat gttcaagcct ggcgaaatct atacggcgca aaagttgaaa tcatcaaccg   40380
gatcttttta cgtcagcaac agtaaagggc atcgcatgtt cctgaacggc ggcgaaggca   40440
ctaaggttat ggcgcacgct atggtgattg ctgaatttga ggaagtgaaa gatggaaaca   40500
aataagcgcg ttaaacacaa gtttattgat aatcatggcg atgcacttga ggtatacaag   40560
ttcggcgatc gcgtgtttat tgatggcacg tttcaaggtg aagcatgcc ggattttagg    40620 tcaatactca ccattgacca ggtgcgcaag ctggcggata agttaaatga tctggcagat   40680
gaaatcgaat acaagcaaat tcattttaat tgataggttt gataatgaaa aaatacgaat   40740
ttgaactttg gggcagcaaa taccattttt ccacgagcaa gccgattgtt atcgttgacc   40800
tggacggaac gttatcagac ggatcgcatc gcttgcacct gcttccgaaa aagatttgc    40860 accttacaga aagctggtct gagttcaata aggcggctgt tggcgattcg ccgattaata   40920
gcacggttgc agtggttaac ggtttgtgga tgtcaggatt tgccatcgtt atcctgaccg   40980
gacgcagcga cgaagtgatg gcggatacct gcaagtggct tagtgaaagc ggcgtcaagt   41040
acgacgcgtt aatcatgcgc cgcaaggaag acaaccgcaa agacacgatc atcaaagaag   41100
aagtattgcg cgctattggc ctggacaaca ttgtgtgcgc ttttgatgat tcacctaacg   41160
tggttaagca cttccgcagc ctgggaatca caacctatca ggtcacggaa tacgataagc   41220
cacataatca tatccaatcg catggcgtgg aggaattgca gaaatgatcc tgaaagtagc   41280
atatgctaac cctcgcggct gcaatatata cggctttaag gttggcgcga tggtcaacgc   41340
caggataaac gaaaaaggcg tattagttgt caagtctcct aaaactggca tggatatgcg   41400
catcaaggag aacggcggaa gattgtttat caggtcaatg gctggtcaaa cgctcgcaac   41460
gttcacaaaa tagcactttt tgcaaaaaca gattgtcggg cttgcggtat agtaagccca   41520
tcgacaacaa acgaggatta atcatggtt aataaagttg agttttcaa agcggtagac     41580 aagattgacg gcgcgcaaag tttctttgct atccattcca ttgacggcga agacgttgca   41640
tacaacgtga ttagtcgaga cggtatatca aaacttagtg acctggtggg ttatattgtg   41700
gcgaacggga aatgtgcatg gcccgatttg ccacgagagc cgcgccgccg agacatgcaa   41760
aatccagtcc tgctttacac gctggtaatt gaaggagtca acaaatgatt tggttacttg   41820
tatttttggt ggttttcttt tatatttcag gcttattcat cttccgtgcg ctggtgaaaa   41880
catgcgattg cacggataaa gatcagcctc ttgttctgat gttctggttt gtgtggtttt   41940
gggtggcgct ttaccagatt gtacgggatg aaagcggctt taagtggtga ttcttactat   42000
agcgcattca cgcagtgcgc tatgttgaga taacaacatg agatcatgaa gatgcgaaac   42060
ttcgaaaaaa atcgtatcca aaaagaagcg atacagctac cacgagcacc aagagatgaa   42120
tcaacgctat cgcaataagc gccagagcaa aggtaaacat tccggtaaac atggagaaaa   42180
tcaatatgaa acgagacatt atcatcctta acggaccgcc aggagttggc aaagatacgc   42240
ttgcggcata cttaacgggt catcgttacg cagcggttaa agcgtcgttt aagcaaccga   42300
tgtttgatat tgcattctcc atgcttggcg tttaccgata tgacgagttc attgatctgt   42360
ataacgaccg cgagcagaaa gaaaagcctc aagcaatctt gcaaggtaag tcgccgcgac   42420
aattcatgat ctggattagc gaagaagtca tgaagccagc ttttggcgag caatatttcg   42480
gaaatcgcat ggttgagcaa gtacacgaga tgtacagaga tttggctgtt gtaattagtg   42540
atggcggatt ccctgaagaa atcaagccgc tcgttaaggc aggccatgag gttcacattt   42600
gccgactgca tcgcgaagga ttcacgtttg atggagattc gcgaaactat attgacctga   42660
gcggatacca tcacagagtc aaacattacg acttcacaat gactgatggc gagccagaaa   42720
```

```
agactgttga cgagatcatc aaaactgtcc agtggaaaca cattaagatc aaatagcacg    42780
aattgctaaa agcggggcgc aatgcctcgc tataatgcaa acaccaatca acgagaggaa    42840
atcatcatgg tagagttaaa cgacattcgc gttggaacaa aatttcgcgt aacctgggca    42900
gataaatatt gcggagttag caagggccag gttgttactg tggatagtat ttatcgcgga    42960
tgcagcaaag actttcgccg cccacgcatc aagaatggct atatcattac tcgacgtttt    43020
ggctttgagt gttattgcgt agtggcgact caaggagttt tgattgagct tcagcgaatt    43080
agcgatcatc gcggctgtca tgtcaaaaca acgaagatac catctcagcg atcgcgatac    43140
gatgcgcgac ggatgcgccg actcgctcga atgcgatca agttcaagaa gcatggtggt    43200 aactttacc gaatgtacaa agggattgcg cgaaatgctg aaaataaca acaacgcaac    43260 caacccaaag ccgccatttg attttcatga aatcatgatt gtgttattct tgattctctt    43320
agttgtttat tcagtgaggg ccgcaatatg gttttaatg cactaaaacg aatctttaaa    43380
cctgaatacc ggatcgttgc ttgcacagaa tgcaagattt attatctgca acgccgccgc    43440
gttattagtg gggattggga atatctgacg gatgatgctt tcggcttttg ggctatggag    43500
ttcaatagct acagcgaagc gcgtgagtac gctaaaaagt tgcacaagtt cagaccttac    43560
aagctgcgtt tgctggttgt caaaaaatgc gatgtgtggg atcacgtatg aaaagagtaa    43620
ttataacttt tattgctctt atcgctggtt ctcacttggc ttatgggtat agcggcattg    43680
tcgagtcaat cggcggaatg attatcttcc tggctggcgc atgttacggc tacggcgatg    43740
gatttaaaaa tggcaagcgt tacatcctga ctggcaagaa ataatgttaa ccgcgccgct    43800
tcggtggcgc taaaggagg aaacaaaatg gctaaaagca atcgtaaaat gttgattaac    43860
gcattcgaaa aggcagcgct tgagcgtggt tggaatgact catttcacac agcaaactgt    43920
atccgccgtt acggattcaa gaattgccgc tcctgggcgc gtcaaatggc ttcatggtat    43980
gatcttgatg cgcattacct tgatatggat tgcgccctgg ttgaaatgat tgagcaggca    44040
gcgttagagg atcgaccatt aacgcaatcc gattttgacg attttgttcg cgatgaaatc    44100
tattacatga gctaatagca cttttttgtta aaacttccgc gagggcattt gttaaagtgt    44160
cctcattgaa gcgaaacaga ggaaaacaaa atgaaaattc gaatcaccag ggttgacatt    44220
gaccgcaatg acggaagcat tacccttgag caatgcggat tcaaagttgg tgacattgta    44280
gaggttgacg gattctttcg cgatggttct tactgcgtgt tagcaatccg caacacggaa    44340
gaaattcgaa tcggtgataa catcggcgta aaccatgacg aatgcgaggt agtagaggaa    44400
tgatcacgat taacctttca gaagagcaag caaagaaact cctgcatgct gtaggttctc    44460
gtgcactttg cggatcaact gatgaaatga tgattgatca tgaggttgca agggagcttt    44520
ttactcagct tgagcaaaaa ttctcaccac gtccgactga cacggcagaa actgcaaaat    44580
ggcttgctga gaatggatac acggctttaa aagttcacaa ctggaagcga aaaacgaagc    44640
gttggagaat gctggatttt aattaaaatt gaatgcctca tacagcgaac aggacgcatt    44700
ttgacgaggc atttttttagg taaggtgatt caatggataa ctacataaaa ccgtcgcagt    44760
ggtgcgcaca gaagcaagag gaagcattag agcgcggcga tactgaaaca gcaatgcact    44820
atttcgaaat gtacaacttg tggaagggta gaggtctgta atgtttggaa tgaacgaggc    44880
gcaattcaac gctgcaaaac gccaggctaa gaagtgcggc gaggcaatga aggcggatgt    44940
tgaaaagcgc gggaagtatg ttgatgaagt catgaagggc attattgccg aacattatca    45000
gccagttgcg ccaatgctga caattaccca attcatctgg ttgtgtggtt atcttcgtgg    45060
```

-continued

```
tagatgggga aacgcatttg accgcgaatg attgacaacg atttcctgat tggttagcat    45120
attcagcgtt tacataagag cggcattagt gccgaacggg tggcgcggct gccacgcaac    45180
aacggcgata tgcaggtttt taccgtaaga cgtatcgcct ttttaatagg tgaatatatg    45240
gaaaagtaca aattaacttt catgtttgac aatatggtga tgaatccctt aaatggttac    45300
gcttgcaata gcttttctgt taccgtgaat gcggatgaaa ttgaggatga tggcaaattt    45360
atcctaatag gtgattacat ttatcctatt cacaatatca attgcatcaa acgcgagatc    45420
gtaaaagatg aagtacaatg taagattgac gatcaggcga atgggcgta attgctcgtc     45480
atgtagacag agttttgaat gtgaggttga ggcgcgcgga gagcttgagg cagcagcaag    45540
agcaaaagag ttgtccggcg ctaatcaaga cactcaccag ttttcaatag atcttgtaag    45600
gaaaatatca tgagttctgt aattattggt ttggttgctt taatcattgg tgttctaatc    45660
ggctttgtcg ctgtatcttt cgtggtggct gttggtgttc gctataagtc aaaaaaaggt    45720
gaatttgctt tagcgttttg ggatgaagag cagaaagttt ggcaggttcg cggtcactat    45780
ttatcaatcg gtggcaggat tcacagcact atgaaaacaa atccagaaaa agtaaaatac    45840
aagtattgac caactacccg ccaaatggcg ggtttttat tgcctgcaat ttgtctataa     45900
tgaggctttg ttataaagga gggcgcatta tggctaaaaa cgttgagcca gcagtaaagg    45960
cttgcaattt taaaaaacta tataataagc aatatggcga tatagcaaaa atgacaaagg    46020
cgcacaagta cacgccggaa caggtgtttg atctggctgt tcgttacttt acgtgggctg    46080
aggaaaacca tatacaggct gcggaaacgg catcctttca gggtgacgta tacgaaagca    46140
agattcacaa gccgcgcgtg ttcaccttaa acggattccg attattcgct ggcctttctg    46200
cctccgtgct tgaaaaatgg cgacgcgagc caggatttag cgatgttatg gactttatcg    46260
acggcgttgt ttacgagcaa aaattccagc ttgctgcaaa caatattgtt aacgccggat    46320
tcattggtaa agagatcggc attgaaaagc cagccaccgt taccattgag aataacacaa    46380
gcgccagcgt tgacgctgta acggcggagg aagtcaaaga ggcggtaatt gacattctgg    46440
agaagatata atgctgattt gggaagactt aacagcggcg caaaaacgcg ccattaagga    46500
aatgagcgaa tattcattcg aaaagatgat ccgcatttgg tttcaacttc tccaggggca    46560
aaggttttta ggaaactggc atttcagcta cctatgcagc gaagttgaaa aaatcatcaa    46620
aggcgagtca cagaatgtaa ttttcaacat aacgccaggc agtggtaaaa cagagatatt    46680
ctcgatccac atgtcacctt atgcgtcatt gaaaagtaag aaggtgagaa atcttaatttt   46740
gtcgtttagt gatggacttg tccagcagaa tagcaaccgc attaaggaga ttattggttc    46800
tccagaatgg caggagctat ggcctggaaa gttggcaaag gcgagcgcaa aggatttgat    46860
tgtaacagat ggcggcaagg ttaaattaca agtcaactcg cgttctattg gtggtcaggt    46920
tactggtctg cgtggcggct acatggacga tggttttact ggtatgctgg ttcttgacga    46980
tccagacaag ccggatgaca tgcttttctaa ggtgaagcgc gaagccggac acatgcgcct   47040
aaagaacacg gtgcgatcgc gtcgaatgaa ggacaccacg ccaattgtga tggttcaaca    47100
acggctacac gtcaatgatt caacgtggtt catgacaaac ggcggcatgg gcggcatcca    47160
gtttaaggtg gttagtattc cggcgctcgt tactaaggaa tatcgcgaaa cgcttcctga    47220
ttggttaaag cctgagtttg atcgcgatgt tttgtccagt aatccagtga tgattgatgg    47280
tgttgctcat tattcgttct ggcctgctaa ggaaagcgcg gaggaattac ttgcacttcg    47340
aaatgctgat ccgtacacgt tcgccagtca gtatcagcaa cagcctgttg cgcttggtgg    47400
taacgtgttt aaaacagagt ggttccagta ttacggcagc agcgagaaat gcacgctacc    47460
```

```
aaaaccggat cgctttgaat atacatttat cacggttgat accgcgcaga aaacaggtga   47520
gcttaacgac tactccgtga tctgttattg ggggatgtat aaagatcgtg tctacttcat   47580
tgatggcgtt cgcggaaaat gggaagcacc ggaccttgag acgaattttg ttgcattcgt   47640
taatcagtgc tggaagcgca ataaagaatg cggaacgttg cgaaggattc atgttgaaga   47700
taaatcatct ggcactggct tgattcagag tgcagcgaaa aaaatcatga tcaagatcaa   47760
tcccgttcag cgcgataaag acaaggttac gcgagcaatg gacgcagcgc cagtaatgcg   47820
cgccggacgc gtagcacttc cagaatccca tcctatgctg gctgagatac tagctgaagt   47880
tgcggcgttt acattcgatg atagccatcc tcatgatgat attgttgata acatcattga   47940
tgcggttaac attgaaatga acatggcaga tgatccggtt ggaagaatga aaaaattggc   48000
aggtttgcgg aacaaatagc acgaatcgac aaaccaatat ataatcaaag ctgaaaaat   48060 ccagccttt ttattggagg aaagataatg agtaaatcac gaatcgttaa ggctgatggc   48120
tataacgaga tctttaaagg cgagaattgc aaatcgcgag tagagcaacc attctacatg   48180
caatcaatgc catacaagac acttgctgac ttttacgaaa aagacggcct ggcaaaaagg   48240
gttattgacg tagtaccaga ggaaatggtt tccctggct tcacggttga cggcgtggca   48300
gacgaggcag cattccgttc tttgtgggat gagaagcgat tgaatgcaaa aattattgat   48360
gcgctttgct ggtcgcgttt gtttggtgga tctgcaatca ttgctcttgt tcaggatggg   48420
cgagcgctca aatcacctgt aaagcctggt gccatgttgg aggatgtgcg agtttacgat   48480
cgctatcaga ttcgcgttga agcgcgcgaa actaatccac gcaaagttcg ctatggtgag   48540
ccagtgcttt acactgtaac gccaggcgga gacttgccgg aataccaggt acactacacg   48600
cgagtttgca ttatcgacgg tgagcggata cctaacgcaa agcgacgcag caatgacggc   48660
tggggtgagt cagttcttaa caagcggctt gttgaggcta ttgttgatta taactattgt   48720
gaaacattag cgacgcaatt attgcgaaga aaacaacagg cagtatgaa ggccaaaggt   48780 cttgctgact tgtgcgatga tgaagaaggt gttagcgcgg cacgcttgag acttgcgcag   48840
gttgacgatg agggcggcgt aggcaaggcc attggtattg atgctgagga tgaggaatat   48900
gatgttctta actctgacat tagcggcgtt gattcttttc tggaaaagaa aatggatcgc   48960
atagtttccc tttcaggtat tcatgaaatc atcctgaaaa ataaaaacgt tggcggcgtt   49020
agcgcaagcc aaaacacggc gcttgaaaca ttctataaac ttattgagcg aaaacgcgtt   49080
gaggattaca agcctatcct tgaatttcta ttaccgttca tcattagtga gcaggagtgg   49140
agcattgagt tttcaccttt gagcgtgcct agcgataaag atcaagctga gattctgaat   49200
aagaatatcg actcaatcag caaggctatt gatggtcagt tccttgatgt tgaagaagcg   49260
cgcgacacgt tgcgagcaat cgccccaagc gttaaactaa aggacactaa taaatcaag   49320 ctgccggagc caactgagcc ggagccaggc acacagggga atgagtaatg aaagtgaaag   49380
gcgttgttaa acaatggcgc tttcctgaag caagcgagcg gcaatttagc cgctcaattc   49440
aggaggcaat cagagatctt gtagttctca tgcgcaagcg aacaaaagcg atgaagtttg   49500
acgcaacaga taatgagatc aacagcgcag aagatgaaat taacagcatg caactgacc   49560 ttatagctgg cattgtttcc actcttcctg caatcgcgtt gaccatttat aaattcaatg   49620
cgaagcagtt tatcaatgtt gccaagtcaa ctggcggaaa ggataatacg gcggtaattg   49680
ttttgatcgc ggttggcgct aacgctaacg aggattggta tcagacgctc tacggtcaat   49740
ggcacgggct tacagaatca tcgctaagga agttattcac aaacattgtt tctgattggt   49800
```

```
caacaaacat tcgcaatgca aactttcgcg gaagcaatga taaacaggtt aatgatcttg    49860
cagaaaagag atttgctgtt tatagctctt ggggtaaaac gagatcagaa aacattatcg    49920
gagcgtggaa tagtcgcctg atgcgccagc gcctttatga tgctaaggta actcattatt    49980
tctggcatgg aatgttagat gacagagagc gcttgcagca tgtgttatgg gaaggtaaaa    50040
gaatagcgct tgatgcaatt catgatttcc ctggtgagcc gtggggttgc cgttgctggg    50100
cgattccaga ttggaatagt aaaggagaat aattaatgaa ggcaaaacaa agatttgata    50160
gcgtccaggt taaggcgcat tttgatgata atggcttttt agtggatcgc ccaattgtgg    50220
cgcgaattgg tttgcaggag taccgcacac cgtatggaat cagacgagag ttcagaccag    50280
cgtccgaggt gttcaaggct gattcccttg ccacattcgc aggtaagccg atcactatcg    50340
gtcacgtcac ggtaacgcca gacaatgcgg atcaggttgt tgttggttca tgcgctggtg    50400
ctggtgttcc aaatggtgtt ggcgttgaag ttccgttaag tatttactca aagcgagcaa    50460
ttgagagcgc aaaaaagaaa gacacggcgg aaatttcagt tggttacaca tcaattgata    50520
ttgataaacc aggttggggc aataataaaa ctggcgatta cttgtttgag gaagacatta    50580
aggaagactg gaagcctgat tcccctgatt gggttaaatt tgacgccatt cagacgaata    50640
tccgtgttaa tcacattgca cttgtctttc gtggtcgtgc tggcattgcc aaattaaatc    50700
ttgatagtga acaagatttt ccgtatagtg acgaggttct aaatgacaaa ggagatgagg    50760
aaatgacagt aaaaattaaa cttgatggcg cggtagaatt tgatgttcca aaggccgttg    50820
ctgatcatat tgaggcgtta aaggcagatg caaaagctgc aaccgaaaaa gctgatggcc    50880
ttgaggccga gcgcgacgcc ctgaaaacta aagtcgatgg cattccggcg cagattgcag    50940
aagctgttaa gaaggcaaag actgacgcag aagaacacgc caagctagtt gcagatgcaa    51000
ctgaaattgg catcaagtgt gacggcttgg acgctaaagc gatcaaagtt gcttacgtca    51060
aagaagtcac tggcgctgat atttcagaaa aagccgatgc at                      51102
```

ESCHERICHIA COLI BACTERIOPHAGE ESC-COP-9 AND USE FOR INHIBITING PROLIFERATION OF PATHOGENIC ESCHERICHIA COLI THEREOF

CROSS-REFERENCE TO RELATED APPLICATIONS

This application is a U.S. National Phase Application of International Application No. PCT/KR2017/010957, filed Sep. 29, 2017, which claims priority to Korean Application No. 10-2016-0161324, filed Nov. 30, 2016, each of which are hereby incorporated by reference in their entirety.

REFERENCE TO SEQUENCE LISTING

The Sequence Listing submitted Dec. 13, 2018 as a text file named "08162 0052U1 Sequence Listing.txt," created on May 29, 2019, and having a size of 65,219 bytes is hereby incorporated by reference pursuant to 37 C.F.R. § 1.52(e)(5).

TECHNICAL FIELD

The present invention relates to a bacteriophage isolated from nature, which infects *Escherichia coli* to thus kill *Escherichia coli*, and a method for preventing and treating a pathogenic *Escherichia coli* infection using a composition including the same as an active ingredient. More particularly, the present invention relates to a Siphoviridae bacteriophage Esc-COP-9 (Accession number: KCTC 13131BP) isolated from nature, which has the ability to specifically kill *Escherichia coli* and which includes a genome expressed by SEQ. ID. NO: 1, and a method for preventing a pathogenic *Escherichia coli* and a treatment method after the pathogenic *Escherichia coli* infection using a composition including the bacteriophage as an active ingredient.

BACKGROUND ART

*Escherichia coli* belongs to the intestinal microflora, is a gram-negative bacillus and a catalase-positive, oxidase-negative, and facultative anaerobic bacterium, and most examples thereof degrade lactose. *Escherichia coli* is serologically subdivided according to whether it contains a somatic (O), flagellar (H) or capsular (K) antigen, and these antigens are known to be associated with the pathogenicity of *Escherichia coli*. Pathogenic *Escherichia coli* refers to *Escherichia coli* that has acquired a small number of the virulence factors capable of being expressed in *Escherichia coli*, and, depending on the onset characteristics and the kind of toxin, there are five types of *Escherichia coli*, namely enterohemorrhagic *Escherichia coli*, enterotoxigenic *Escherichia coli*, enteroinvasive *Escherichia coli*, enteropathogenic *Escherichia coli*, and enteroaggregative *Escherichia coli*. Pathogenic *Escherichia coli* in livestock infects various ages thereof to thus cause disease, and the main symptom thereof is diarrhea, and mortality due to extreme dehydration is very high. Diarrhea caused by pathogenic *Escherichia coli* is known to be the main disease that afflicts almost all livestock farming in Korea, and the damage to the livestock industry is regarded as significant.

Generally, vaccines and antibiotics are used for the prevention and treatment of infectious diseases of pathogenic *Escherichia coli*. Here, the effectiveness of antibiotics has been continuously decreasing due to the increase of antibiotic-resistant bacteria, and the development of effective methods other than antibiotics is required due to the increased number of regulations on the use of antibiotics in animals.

Recently, the use of bacteriophages as a countermeasure against bacterial diseases has attracted considerable attention. In particular, interest in bacteriophages is higher than ever due to the preference for environmentally friendly methods. Bacteriophages are very small microorganisms infecting bacteria, and are usually simply called "phages". Once a bacteriophage infects bacteria, the bacteriophage is proliferated inside the bacterial cell. After proliferation, the progeny of the bacteriophage destroy the bacterial cell wall and escapes from the host bacteria, suggesting that the bacteriophage has the ability to kill bacteria. The manner in which the bacteriophage infects bacteria is characterized by the very high specificity thereof, and thus the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria, but does not affect commensal bacteria in the environment or in animals. Conventional antibiotics, which have been widely used for bacterial treatment, incidentally influence many kinds of bacteria. This causes problems such as environmental pollution and the disturbance of normal flora in animals. On the other hand, the use of bacteriophages does not disturb normal flora in animals, because the target bacterium is selectively killed. Hence, the bacteriophage may be utilized safely, which thus greatly lessens the probability of adverse actions in use compared to any other antibiotics.

Bacteriophages were first discovered by the English bacteriologist Twort in 1915 when he noticed that Micrococcus colonies melted and became transparent by something unknown. In 1917, the French bacteriologist d'Herelle discovered that *Shigella dysenteriae* in the filtrate of dysentery patient feces was melted by something, and further studied this phenomenon. As a result, he independently identified bacteriophages, and named them bacteriophages, which means "eater of bacteria". Since then, various bacteriophages acting against such pathogenic bacteria as *Shigella*, *Salmonella Typhi*, and *Vibrio cholerae* have been continuously identified.

Owing to the unique ability of bacteriophages to kill bacteria, bacteriophages have attracted anticipation as a potentially effective countermeasure against bacterial infection since their discovery, and there has been a lot of research related thereto. However, since penicillin was discovered by Fleming, studies on bacteriophages have continued only in some Eastern European countries and the former Soviet Union, because the spread of antibiotics was generalized. Since 2000, the limitations of conventional antibiotics have appeared due to the increase in antibiotic-resistant bacteria, and the possibility of developing bacteriophages as a substitute for conventional antibiotics has been highlighted, so that bacteriophages are again attracting attention as antibacterial agents. In particular, recently, government regulations for the use of antibiotics have become more stringent around the world, and thus interest in bacteriophages is increasing and the range of industrial applications therefore is continually broadening.

As demonstrated above, bacteriophages tend to be highly specific for bacteria. Because of this specificity, bacteriophages frequently exhibit an antibacterial effect only for certain strains of bacteria, even though the bacteria belong to the same species. In addition, the antibacterial strength of bacteriophages may depend on the type of target bacterial strain. Therefore, it is necessary to collect many kinds of bacteriophages that are useful in order to get effective control of specific bacteria. Hence, in order to develop the effective bacteriophage utilization method in response to pathogenic *Escherichia coli*, many kinds of bacteriophages that exhibit antibacterial action against *Escherichia coli* must be acquired. Furthermore, the resulting bacteriophages need to be screened as to whether or not they are superior to others from the aspect of antibacterial strength and spectrum.

DISCLOSURE

Technical Problem

Therefore, the present inventors endeavored to develop a composition applicable for the prevention or treatment of a pathogenic *Escherichia coli* infection using a bacteriophage that is isolated from nature and is capable of selectively killing *Escherichia coli*, and further to establish a method for preventing or treating a pathogenic *Escherichia coli* infection using the composition. As a result, the present inventors isolated a bacteriophage suitable for this purpose from nature and secured the gene sequence of the genome that distinguishes the isolated bacteriophage from other bacteriophages. Then, the present inventors developed a composition including the bacteriophage as an active ingredient, and identified that this composition is capable of being used to effectively prevent and treat a pathogenic *Escherichia coli* infection, leading to the completion of the present invention.

Accordingly, it is an object of the present invention to provide a Siphoviridae bacteriophage Esc-COP-9 (Accession number: KCTC 13131BP) isolated from nature, which has the ability to specifically kill *Escherichia coli* and which includes the genome expressed by SEQ. ID. NO: 1.

It is another object of the present invention to provide a composition applicable for preventing a pathogenic *Escherichia coli* infection, which includes a bacteriophage Esc-COP-9 infecting *Escherichia coli* to thus kill *Escherichia coli* as an active ingredient, and a method for preventing a pathogenic *Escherichia coli* infection using said composition.

It is another object of the present invention to provide a composition applicable for treating a pathogenic *Escherichia coli* infection, which includes a bacteriophage Esc-COP-9 infecting *Escherichia coli* to thus kill *Escherichia coli* as an active ingredient, and a method for treating a pathogenic *Escherichia coli* infection using said composition.

It is another object of the present invention to provide a disinfectant for preventing and treating a pathogenic *Escherichia coli* infection using said composition.

It is another object of the present invention to provide a drinking-water additive for preventing and treating a pathogenic *Escherichia coli* infection using said composition.

It is another object of the present invention to provide a feed additive effective upon farming by preventing and treating a pathogenic *Escherichia coli* infection using said composition.

Technical Solution

The present invention provides a Siphoviridae bacteriophage Esc-COP-9 (Accession number: KCTC 13131BP) isolated from nature, which has the ability to specifically kill *Escherichia coli* and which includes a genome expressed by SEQ. ID. NO: 1, and a method for preventing and treating a pathogenic *Escherichia coli* infection using a composition including the same as an active ingredient.

The bacteriophage Esc-COP-9 was isolated by the present inventors and then deposited under the Budapest Treaty on the International Procedure at Korea Collection for Type Cultures, Korea Research Institute of Bioscience and Biotechnology (KRIBB), 125 Gwahak-ro, Yuseong-gu, Daijeon 305-806, Republic of Korea; the deposit was made on Oct. 17, 2016 (Accession number: KCTC 13131BP).

The present invention also provides a disinfectant, a drinking-water additive, and a feed additive applicable for the prevention or treatment of a pathogenic *Escherichia coli* infection, which include the bacteriophage Esc-COP-9 as an active ingredient.

Since the bacteriophage Esc-COP-9 included in the composition of the present invention kills *Escherichia coli* effectively, it is considered effective in the prevention (prevention of infection) or treatment (treatment of infection) of diseases caused by pathogenic *Escherichia coli*. Therefore, the composition of the present invention is capable of being utilized for the prevention and treatment of diseases caused by pathogenic Escherichia coli.

In this description, the terms "prevention" and "prevent" indicate (i) to block a pathogenic *Escherichia coli* infection; and (ii) to inhibit the progression of diseases caused by a pathogenic *Escherichia coli* infection.

In this description, the terms "treatment" and "treat" indicate all actions that (i) suppress diseases caused by pathogenic *Escherichia coli*; and (ii) alleviate the pathological condition of the diseases caused by pathogenic *Escherichia coli*.

In this description, the terms "isolate", "isolating", and "isolated" indicate actions which isolate bacteriophages from nature by applying diverse experimental techniques and which secure characteristics that can distinguish the target bacteriophage from others, and further include the action of proliferating the target bacteriophage using bioengineering techniques so that the target bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Esc-COP-9 is included as an active ingredient. The bacteriophage Esc-COP-9 is included at a concentration of $1 \times 10^1$ pfu/ml to $1 \times 10^{30}$ pfu/ml or $\times 10^1$ pfu/g to $\times 10^{30}$ pfu/g, and preferably at a concentration of $1 \times 10^4$ pfu/ml to $1 \times 10^{15}$ pfu/ml or $1 \times 10^4$ pfu/g to $1 \times 10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. Then, the formulation may be in the form of a solution, suspension, or emulsion in oil or a water-soluble medium, extract, powder, granule, tablet, or capsule. A dispersing agent or stabilizer may be additionally included.

The composition of the present invention may be prepared as a disinfectant, a drinking-water additive, and a feed additive according to the purpose of use, without limitation thereto.

In order to improve the effectiveness of above purpose, bacteriophages that confer antibacterial activity against other bacterial species may be further included in the composition of the present invention. In addition, other kinds of bacteriophages that have antibacterial activity against *Escherichia coli* may be further included in the composition of the present invention. These bacteriophages may be combined properly so as to maximize antibacterial effects, because their antibacterial activities against *Escherichia coli* may be different from the aspects of antibacterial strength and spectrum.

Advantageous Effects

The method for preventing and treating a pathogenic *Escherichia coli* infection using the composition including the bacteriophage Esc-COP-9 as an active ingredient according to the present invention may have the advantage of very high specificity for *Escherichia coli*, compared with conventional methods based on chemical materials including existing antibiotics. This means that the composition can be used for preventing or treating a pathogenic *Escherichia coli* infection without affecting other bacteria, namely useful commensal bacteria, and has fewer side effects attributable to the use thereof. In general, when chemical materials such as antibiotics are used, commensal bacteria are also damaged, thus weakening immunity in animals and entailing various side effects owing to the use thereof. Further, the composition of the present invention uses a bacteriophage isolated from nature as an active ingredient, and thus it is very environmentally friendly. Meanwhile, in the case of bacteriophages exhibiting antibacterial activity against the same species of bacteria, each antibacterial activity of the bacteriophages are different with regard to antibacterial strength and spectrum [the spectrum of the antibacterial activity of the bacteriophages applied to individual bacteria strains in terms of the strains of various bacteria belonging to *Escherichia coli*. Typically, bacteriophages are usually effective only on some bacterial strains, even within the same species. That is to say, the antibacterial activity of bacteriophages may depend on the bacterial strain even for the same species of bacteria]. Accordingly, the present invention may provide antibacterial activity against *Escherichia coli* different to that provided by other bacteriophages acting on *Escherichia coli*. This provides significantly different applicability to industrial fields.

DESCRIPTION OF DRAWINGS

FIG. 1 is an electron micrograph showing the morphology of the bacteriophage Esc-COP-9.

FIG. 2 is a photograph showing the results of an experiment on the ability of the bacteriophage Esc-COP-9 to kill *Escherichia coli*. The clear zone is a plaque formed by lysis of the target bacteria.

MODE FOR INVENTION

Hereinafter, the present invention will be described in more detail with reference to Examples. However, the Examples are merely examples of the present invention, and the scope of the present invention is not limited to the Examples.

Example 1

Isolation of Bacteriophage Capable of Killing *Escherichia coli*

Samples were collected from nature to isolate the bacteriophage capable of killing *Escherichia coli*. Here, the *Escherichia coli* strains used for the bacteriophage isolation had been previously isolated and identified as pathogenic *Escherichia coli* by the present inventors.

The procedure for isolating the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Escherichia coli* at a ratio of 1/1000, followed by shaking culture at 37° C. for 3 to 4 hours. Upon completion of the culture, centrifugation was performed at 8,000 rpm for 20 minutes and a supernatant was recovered. The recovered supernatant was inoculated with *Escherichia coli* at a ratio of 1/1000, followed by shaking culture at 37° C. for 3 to 4 hours. When the sample contained the bacteriophage, the above procedure was repeated a total of 5 times in order to sufficiently increase the number (titer) of the bacteriophage. After repeating the procedure 5 times, the culture solution was subjected to centrifugation at 8,000 rpm for 20 minutes. After the centrifugation, the recovered supernatant was filtered using a 0.45 μm filter. The obtained filtrate was used in a typical spot assay for examining whether or not a bacteriophage capable of killing *Escherichia coli* was included therein.

The spot assay was performed as follows: TSB culture medium was inoculated with *Escherichia coli* at a ratio of 1/1000, followed by shaking culture at 37° C. overnight. 3 ml (OD600 of 1.5) of the culture solution of *Escherichia coli* prepared above was spread on TSA (casein digest, 15 g/L; soybean digest, 5 g/L; NaCl, 5 g/L; agar, 15 g/L) plate. The plate was left on a clean bench for about 30 minutes to dry the spread solution. After drying, 10 μl of the prepared filtrate was spotted onto the plate culture medium on which *Escherichia coli* was spread and then left to dry for about 30 minutes. After drying, the plate culture medium that was subjected to spotting was stationary-cultured at 37° C. for one day, and then examined for the formation of clear zones at the positions where the filtrate was dropped. In the case of the filtrate generated a clear zone, it is judged that the bacteriophage capable of killing *Escherichia coli* is included therein. Through the above examination, the filtrate containing the bacteriophage having the ability to kill *Escherichia coli* could be obtained.

The pure bacteriophage was isolated from the filtrate confirmed above to have the bacteriophage capable of killing *Escherichia coli*. A conventional plaque assay was used to isolate the pure bacteriophage. In detail, a plaque formed in the course of the plaque assay was recovered using a sterilized tip, which was then added to the culture solution of *Escherichia coli*, followed by culturing at 37° C. for 4 to 5 hours. After the culturing, centrifugation was performed at 8,000 rpm for 20 minutes to obtain a supernatant. The *Escherichia coli* culture solution was added to the obtained supernatant at a volume ratio of 1/50, followed by culturing at 37° C. for 4 to 5 hours. In order to increase the number of bacteriophages, the above procedure was repeated at least 5 times. Then, centrifugation was performed at 8,000 rpm for 20 minutes in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, a solution containing the pure bacteriophage was obtained. The procedure for isolating the pure bacteriophage was generally repeated until the generated plaques became similar to each other in size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage isolated above was confirmed to belong to the Siphoviridae bacteriophage.

The solution containing the pure bacteriophage confirmed above was subjected to the following purification process. The *Escherichia coli* culture solution was added to the solution containing the pure bacteriophage at a volume ratio of 1/50 based on the total volume of the bacteriophage solution, followed by further culturing for 4 to 5 hours. After the culturing, centrifugation was performed at 8,000 rpm for 20 minutes to obtain a supernatant. This procedure was repeated a total of 5 times in order to obtain a solution containing sufficient numbers of the bacteriophage. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% gelatin, pH 8.0). The resulting material was referred to as a bacteriophage suspension or bacteriophage solution.

As a result, the pure bacteriophage purified above was collected, was named the bacteriophage Esc-COP-9, and then deposited at Korea Collection for Type Culture, Korea Research Institute of Bioscience and Biotechnology on Oct. 17, 2016 (Accession number: KCTC 13131BP).

Example 2

Separation and Sequence Analysis of Genome of Bacteriophage Esc-COP-9

The genome of the bacteriophage Esc-COP-9 was separated as follows. The genome was separated from the bacteriophage suspension obtained using the same method as in Example 1. First, in order to remove DNA and RNA of *Escherichia coli* included in the suspension, 200 U of each of DNase I and RNase A was added to 10 ml of the bacteriophage suspension and then left at 37° C. for 30 minutes. After being left for 30 minutes, in order to stop the DNase I and RNase A activity, 500 μl of 0.5 M ethylenediaminetetraacetic acid (EDTA) was added thereto and then left for 10 minutes. In addition, the resulting mixture was further left at 65° C. for 10 minutes, and 100 μl of proteinase K (20 mg/ml) was then added thereto so as to break the outer wall of the bacteriophage, followed by reaction at 37° C. for 20 minutes. After that, 500 μl of 10% sodium dodecyl sulfate (SDS) was added thereto, followed by reaction at 65° C. for 1 hour. After reaction for 1 hour, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes in order to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the genome of the bacteriophage Esc-COP-9.

Information on the sequence of the genome of the bacteriophage Esc-COP-9 obtained above was secured by performing next-generation sequencing analysis using Illumina Mi-Seq equipment from the National Instrumentation Center for Environmental Management, Seoul National University. The finally analyzed genome of the bacteriophage Esc-COP-9 had a size of 51,102 bp, and the sequence of whole genome was expressed by SEQ. ID. NO: 1.

The homology (similarity) of the bacteriophage Esc-COP-9 genomic sequence obtained above with previously reported bacteriophage genomic sequences was investigated using BLAST (http://www.ncbi.nlm.nih.gov/BLAST/) on the web. As a result of the BLAST investigation, the genomic sequence of the bacteriophage Esc-COP-9 was found to have a relatively high homology with the sequence of the Shigella bacteriophage pSf-1 (Genbank Accession No. KC710998.1) (identity: 93%). However, the bacteriophage Esc-COP-9 has an annular genome and *Shigella* bacteriophage pSf-1 has a linear genome, and thus there is a significant difference in the genomic shape therebetween, and the number of open reading frames (ORFs) on the bacteriophage Esc-COP-9 genome is 89, whereas *Shigella* bacteriophage pSf-1 has 94 open reading frames, unlike the bacteriophage Esc-COP-9.

Based upon this result, it is concluded that the bacteriophage Esc-COP-9 must be a novel bacteriophage different from conventionally reported bacteriophages. Further, since the antibacterial strength and spectrum of bacteriophages typically depend on the type of bacteriophage, it is considered that the bacteriophage Esc-COP-9 can provide antibacterial activity different from that of any other bacteriophages reported previously.

Example 3

Investigation Of Ability of Bacteriophage Esc-COP-9 to Kill Pathogenic *Escherichia Coli*

The ability of the isolated bacteriophage Esc-COP-9 to kill pathogenic *Escherichia coli* was investigated. In order to investigate the killing ability, the formation of clear zones was observed using the spot assay in the same manner as described in Example 1. A total of 10 strains that had been isolated and identified as pathogenic *Escherichia coli* by the present inventors were used as pathogenic *Escherichia coli* for the investigation of killing ability. The bacteriophage Esc-COP-9 had the ability to kill a total of 9 strains among 10 strains of pathogenic *Escherichia coli* as the experimental target. The experimental result thereof is shown in FIG. 2. Meanwhile, the ability of the bacteriophage Esc-COP-9 to kill *Bordetella bronchiseptica, Enterococcus faecalis, Enterococcus faecium, Streptococcus mitis, Streptococcus uberis* and *Pseudomonas aeruginosa* was also investigated in a separate experiment. As a result, the bacteriophage Esc-COP-9 did not have the ability to kill these microorganisms.

Therefore, it is confirmed that the bacteriophage Esc-COP-9 has strong ability to kill pathogenic *Escherichia coli* and a broad antibacterial spectrum against pathogenic *Escherichia coli*, suggesting that the bacteriophage Esc-COP-9 can be used as an active ingredient of the composition for preventing and treating pathogenic *Escherichia coli* infection.

Example 4

Experimental Example Regarding Prevention of Pathogenic *Escherichia Coli* Infection Using Bacteriophage Esc-COP-9

100 μl of a bacteriophage Esc-COP-9 solution at a level of $1 \times 10^8$ pfu/ml was added to a tube containing 9 ml of a TSB culture medium. To another tube containing 9 ml of a TSB culture medium, only the same amount of TSB culture medium was further added. A pathogenic *Escherichia coli* culture solution was then added to each tube so that absorbance reached about 0.5 at 600 nm. After pathogenic *Escherichia coli* was added, the tubes were transferred to an incubator at 37° C., followed by shaking culture, during which the growth of pathogenic *Escherichia coli* was observed. As presented in Table 1, it was observed that the growth of pathogenic *Escherichia coli* was inhibited in the tube to which the bacteriophage Esc-COP-9 solution was added, while the growth of pathogenic *Escherichia coli* was not inhibited in the tube to which the bacteriophage solution was not added.

TABLE 1

Growth inhibition of pathogenic *Escherichia coli*

| Classification | $OD_{600}$ absorbance value | | |
| --- | --- | --- | --- |
| | 0 minutes after culture | 30 minutes after culture | 60 minutes after culture |
| Bacteriophage solution is not added | 0.5 | 0.7 | 1.5 |
| Bacteriophage solution is added | 0.5 | 0.3 | 0.1 |

The above results indicate that the bacteriophage Esc-COP-9 of the present invention not only inhibits the growth of pathogenic *Escherichia coli* but also has the ability to kill pathogenic *Escherichia coli*. Therefore, it is concluded that the bacteriophage Esc-COP-9 can be used as an active ingredient of the composition for preventing a pathogenic *Escherichia coli* infection.

Example 5

Example of Treatment of Infectious Diseases of Pathogenic *Escherichia coli* Using Bacteriophage Esc-COP-9

The therapeutic effect of the bacteriophage Esc-COP-9 on pigs afflicted with pathogenic *Escherichia coli* was investigated. A total of 2 groups of four 25-day-old weaning pigs per group were prepared and reared separately in experimental farming pig pens (1.1 m×1.0 m), and the experiment was performed for 14 days. The environment surrounding the pens under the warming facility was controlled, and the temperature and humidity in the pig pens were maintained constant, and the floor of the pig pen was cleaned every day. On the 7th day after the start of the experiment, all pigs were orally administered with a pathogenic *Escherichia coli* solution using an oral injection tube. The administered pathogenic *Escherichia coli* solution was prepared as follows. Pathogenic *Escherichia coli* was cultured at 37° C. for 18 hours using a TSB culture medium, after which the bacteria were isolated and adjusted to $10^9$ CFU/ml using physiological saline (pH 7.2). From the day following administration of the pathogenic *Escherichia coli*, the bacteriophage Esc-COP-9 of $10^9$ PFU was orally administered to the pigs in the experimental group (bacteriophage solution-administered group) twice a day in the same manner as the administration of the pathogenic *Escherichia coli* solution. The pigs in the control group (the group not administered with bacteriophage solution) were not subjected to any treatment. Feed and drinking water were provided to both the control and experimental groups. Diarrhea was examined in all test animals on a daily basis after administration of the pathogenic *Escherichia coli*. The extent of diarrhea was determined by measuring according to a diarrhea index. The diarrhea index was measured using a commonly used Fecal Consistency (FC) score (normal: 0, soft stool: 1, loose diarrhea: 2, severe diarrhea: 3). The results are shown in Table 2.

TABLE 2

Result of measurement of diarrhea index

| | Days after administration with pathogenic *E. coli* | | | | | | |
| --- | --- | --- | --- | --- | --- | --- | --- |
| | 0 | 1 | 2 | 3 | 4 | 5 | 6 |
| Control group (bacteriophage solution not administered) | 1.0 | 1.5 | 1.5 | 1.5 | 1.25 | 1.0 | 0.75 |
| Experimental group (administered with bacteriophage solution) | 0.5 | 0.5 | 0.5 | 0.25 | 0 | 0 | 0 |

From the above results, it is confirmed that the bacteriophage Esc-COP-9 of the present invention could be potentially very effective in the treatment of infectious diseases caused by pathogenic *Escherichia coli*.

Example 6

Preparation of Feed Additives and Feed

Feed additives were prepared using a bacteriophage Esc-COP-9 solution so that a bacteriophage Esc-COP-9 was contained in an amount of $1 \times 10^9$ pfu for 1 g of the feed additives. The method of preparing the feed additives was as follows: Maltodextrin (50%, w/v) was added to the bacteriophage solution, and the resulting mixture was then freeze-dried. Finally, the dried mixture was ground into fine powder. In the above-described preparation procedure, the drying procedure can be replaced with drying under reduced pressure, drying with heat, or drying at room temperature. In order to prepare the control for comparison, the feed additives that did not contain the bacteriophage but contained a buffer (10 mM Tris-HCl, 10 mM MgSO4, 0.1% gelatin, pH 8.0) used to prepare the bacteriophage solution was prepared.

The two kinds of feed additives thus prepared were each mixed with a pig-based feed at a weight ratio of 1,000, thus ultimately preparing two kinds of feed.

Example 7

Preparation of Drinking-Water Additives and Disinfectants

Drinking-water additives and disinfectants were prepared in the same manner because they differ only in utilization and are the same in dosage form. The drinking-water additives (or disinfectants) were prepared using a bacteriophage Esc-COP-9 solution so that a bacteriophage Esc-COP-9 was contained in an amount of $1 \times 10^9$ pfu for 1 ml of the drinking-water additives (or disinfectants). In the method of preparing the drinking-water additives (or disinfectants), the bacteriophage Esc-COP-9 solution was added so that the bacteriophage Esc-COP-9 was contained in an amount of $1 \times 10^9$ pfu for 1 ml of the buffer used to prepare the bacteriophage solution, and mixing was sufficiently performed. In order to prepare the control for comparison, the buffer used to prepare the bacteriophage solution itself was used as the drinking-water additive (or disinfectant) that did not contain the bacteriophage.

The prepared two kinds of drinking-water additives (or disinfectants) were diluted with water at a volume ratio of 1,000, thus ultimately preparing drinking-water additives (or disinfectants).

Example 8

Confirmation of Feeding Effect on Pig Farming

Improvement in pig farming as the result of feeding was investigated using the feed, drinking water or disinfectant prepared in Examples 6 and 7. In particular, the investigation was focused on mortality. A total of 30 piglets were divided into three groups, each including 10 piglets (group A: fed with the feed, group B: fed with the drinking water, and group C: treated with the disinfectant), and an experiment was performed for four weeks. Each group was divided into sub-groups each including 5 piglets, and the sub-groups were classified into a sub-group to which the bacteriophage Esc-COP-9 was applied (sub-group-①) and a sub-group to which the bacteriophage was not applied (sub-group-②). In the present experiment, the target piglets were 20-day-old weaning piglets, and the piglets of the experimental sub-groups were farmed in separate pens placed apart from each other at a certain space interval. The sub-groups were classified and named as shown in Table 3.

TABLE 3

Sub-group classification and expression in pig feeding experiment

| Application | Sub-group classification and expression | |
|---|---|---|
| | Bacteriophage Esc-COP-9 is applied | Bacteriophage is not applied |
| Group fed with feed | A-① | A-② |
| Group fed with drinking water | B-① | B-② |
| Group treated with disinfectant | C-① | C-② |

In the case of provision of the feed, the feed prepared in Example 6 was provided according to a conventional feeding method as classified in Table 3, and the drinking water prepared in Example 7 was provided according to a conventional drinking-water feeding method as classified in Table 3. In the case of disinfection, the disinfection was carried out alternately with the existing disinfection 3 times a week. Disinfection using a typical disinfectant was not performed on the day at which the disinfectant of the present invention was sprayed. The experimental results are shown in Table 4.

TABLE 4

| Group | Mortality (%) |
|---|---|
| A-① | 0 |
| A-② | 60 |
| B-① | 0 |
| B-② | 60 |
| C-① | 0 |
| C-② | 60 |

The above results indicate that the provision of the feed and the drinking water prepared according to the present invention and the disinfection according to the present invention were effective in reducing mortality upon pig farming. Therefore, it is concluded that the composition of the present invention is capable of being effectively applied to improving the results of pig feeding.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

The invention claimed is:

1. A method for treating a pathogenic *Escherichia coli* infection, the method comprising:

administering to an animal other than a human a composition including the Siphoviridae bacteriophage Esc-COP-9 (Accession number: KCTC 13131BP) that can kill pathogenic *Escherichia coli* specifically, which has the genome represented by SEQ. ID. NO: 1, as an active ingredient.

2. The method for treating the pathogenic *Escherichia coli* infection of claim 1, wherein said composition is administered to the animal other than the human for use of a feed additive, a drinking-water additive, or a disinfectant.

* * * * *